United States Patent
Chen et al.

(10) Patent No.: US 11,371,049 B2
(45) Date of Patent: Jun. 28, 2022

(54) ABIOTIC STRESS TOLERANT PLANTS AND POLYNUCLEOTIDES TO IMPROVE ABIOTIC STRESS AND METHODS

(71) Applicants: SINOBIOWAY BIO-AGRICULTURE GROUP CO LTD., Beijing (CN); PIONEER OVERSEAS CORPORATION, Johnston, IA (US)

(72) Inventors: Guangwu Chen, Beijing (CN); Yang Gao, Beijing (CN); Guihua Lu, Beijing (CN); Guanfan Mao, Beijing (CN); Changgui Wang, Beijing (CN); Guokui Wang, Beijing (CN); Yu Zhang, Beijing (CN)

(73) Assignees: SINOBIOWAY BIO-AGRICULTURE GROUP CO LTD; PIONEER OVERSEAS CORPORATION

( * ) Notice: Subject to any disclaimer, the term of this patent is extended or adjusted under 35 U.S.C. 154(b) by 17 days.

(21) Appl. No.: 16/760,340

(22) PCT Filed: Nov. 1, 2018

(86) PCT No.: PCT/CN2018/113323
§ 371 (c)(1),
(2) Date: Apr. 29, 2020

(87) PCT Pub. No.: WO2019/085961
PCT Pub. Date: May 9, 2019

(65) Prior Publication Data
US 2021/0180074 A1    Jun. 17, 2021

(30) Foreign Application Priority Data
Nov. 2, 2017    (CN) .......................... 201711062556.3

(51) Int. Cl.
*C12N 15/82* (2006.01)
*C12N 9/22* (2006.01)

(52) U.S. Cl.
CPC .......... *C12N 15/8201* (2013.01); *C12N 9/22* (2013.01); *C12N 15/8273* (2013.01); *C12N 2310/20* (2017.05)

(58) Field of Classification Search
None
See application file for complete search history.

(56) References Cited

U.S. PATENT DOCUMENTS

| 8,329,991 | B2 | 12/2012 | Shirley et al. |
| 9,428,761 | B2 * | 8/2016 | Broekaert .......... C12N 15/8261 |
| 2006/0123505 | A1 | 6/2006 | Kikuchi et al. |
| 2016/0319296 | A1 | 11/2016 | Gao et al. |

FOREIGN PATENT DOCUMENTS

CN    104450640    3/2015

OTHER PUBLICATIONS

Sequence Accession | 1PWF4_ORYGL, Jun. 13, 2012 (Year: 2012), attached as sequence alignment at the end of the office action.*
International Search Report and Written Opinion PCT/CN2018/113323, dated Jan. 30, 2019.

* cited by examiner

*Primary Examiner* — Elizabeth F McElwain

(57) ABSTRACT

Isolated polynucleotides and polypeptides, and recombinant DNA constructs are useful for conferring improved drought tolerance. Compositions (such as plants or seeds) comprising these recombinant DNA constructs; and methods utilizing these recombinant DNA constructs. The recombinant DNA constructs comprise a polynucleotide operably linked to a promoter that is functional in a plant, wherein said polynucleotides encode drought tolerance polypeptides.

12 Claims, No Drawings
Specification includes a Sequence Listing.

SEQUENCE LISTING

```
<160> NUMBER OF SEQ ID NOS: 42

<210> SEQ ID NO 1
<211> LENGTH: 387
<212> TYPE: DNA
<213> ORGANISM: Oryza sativa

<400> SEQUENCE: 1
gatagtaatt aagagaccat ggtggagtgc caccaccagt acaccaacag catgaaggag     60
aagaggccgc caccgaggag aggtcagctc aagcggcaga tcgcgaggac cttgagcaac    120
ctcatggtgc cgggcggcgg caagcagatc gcagcaggtt cagaggaggg ccaggctgca    180
gcaaaagctc atggatgctt caggcttaga tgatgaattg atggggagag tatggctgat    240
tcaggttcag gcttagatga tgttagttgt taatctattt tgtactatag tcgttagttt    300
```

```
ttgctttcag aacctctctt tgatatccta tataatgctg tgtttgcaat cttgggttcc      360
caacgtatat aggagtagtg cgcacag                                          387
```

<210> SEQ ID NO 2
<211> LENGTH: 201
<212> TYPE: DNA
<213> ORGANISM: Oryza sativa

<400> SEQUENCE: 2

```
atggtggagt gccaccacca gtacaccaac agcatgaagg agaagaggcc gccaccgagg       60
agaggtcagc tcaagcggca gatcgcgagg accttgagca acctcatggt gccgggcggc      120
ggcaagcaga tcgcagcaga acctctcttt gatatcctat ataatgctgt gtttgcaatc      180
ttgggttccc aacgtatata g                                                201
```

<210> SEQ ID NO 3
<211> LENGTH: 66
<212> TYPE: PRT
<213> ORGANISM: Oryza sativa

<400> SEQUENCE: 3

```
Met Val Glu Cys His His Gln Tyr Thr Asn Ser Met Lys Glu Lys Arg
1               5                   10                  15

Pro Pro Arg Arg Gly Gln Leu Lys Arg Gln Ile Ala Arg Thr Leu
            20                  25                  30

Ser Asn Leu Met Val Pro Gly Gly Gly Lys Gln Ile Ala Ala Glu Pro
        35                  40                  45

Leu Phe Asp Ile Leu Tyr Asn Ala Val Phe Ala Ile Leu Gly Ser Gln
    50                  55                  60

Arg Ile
65
```

<210> SEQ ID NO 4
<211> LENGTH: 1417
<212> TYPE: DNA
<213> ORGANISM: Oryza sativa

<400> SEQUENCE: 4

```
ctctgcgtgc aaattccgtc ttccctcgct cctgatctcc atggaagaga agaagcagca       60
gcagcagcgt ccacagagag gcgcgatggc atcctgcag tatccgcacc ttttcttcgc       120
ggcgctggcg ctggccctgc tcctcaccga cccgttccac ctcggcccgc tcgccggggt      180
ggactaccgg ccggtgaggc acgagctggc gccgtaccgc gaggtgatgg cgcggtggcc      240
gcgggacaac ggcagccggc tcaggcacgg caggctggag ttcgtcggag aggtgttcgg      300
gccggagtcc atcgagttcg accgccacgg ccgcggcccc tacgccggcc tcgccgacgg      360
ccgcgtcgtg cggtggatgg gggaggacgc cgggtgggag acgttcgccg tcatgagccc      420
tgactggtcg gagaaagttt gtgccaatgg ggtggagtcg acgacgaaga agcagcacga      480
gatggagcga cggtgcggcc ggcctctcgg gctgaggttt cacggcgaga ccggcgagct      540
ctacgtcgcc gacgcgtact acgggctcat gtccgtcggt ccgaacggcg gggtggcgac      600
ctctctcgcg agagaagtcg gcgggagccc ggtcaacttc gcgaacgacc tcgacatcca      660
ccgcaacggc tccgtgttct tcaccgacac gagcacgaga tacaacagaa aggatcatct      720
gaacgttctg ctagaaggtg aaggcacagg gaggctgctc agatatgacc cagaaaccaa      780
agctgcccat gtcgtgctga gcgggctggt cttcccgaat ggcgtgcaga tttctgacga      840
```

```
ccagcagttc ctcctcttct ccgaaacaac aaactgcagg ataatgcggt actggctgga      900
agggccaaga gccgggcagg tggaggtgtt cgccgacctg ccggggttcc cggacaacgt      960
gcgactgagc agcggcggcg gcggcggacg gttctgggtg gcgatcgact gctgcaggac     1020
ggcggcgcag gaggtgttcg ccaagcggcc gtggctgcga acgctctact tcaagctgcc     1080
cctgacgatg cggacgctgg ggaagatggt cagcatgcgg atgcacaccc tcgtcgcgct     1140
cctcgacggc aaggggacg tcgtcgaggt gctcgaggac cggggcggcg aggtgatgcg     1200
gctggtgagc gaggtgaggg aggtggggcg caagctgtgg atcggcaccg tggctcataa     1260
ccacatcgcc acgatccctt acccgttgga agagcagagt agcagcaacg tgcttggtga     1320
ttgatacttt gataggctgg ttttagcagc aacaaaggtg tactagttga tgtattgttt     1380
gtgtttgccg ggccatcata gaaagtgcct ggtgatc                              1417

<210> SEQ ID NO 5
<211> LENGTH: 1284
<212> TYPE: DNA
<213> ORGANISM: Oryza sativa

<400> SEQUENCE: 5
atggaagaga agaagcagca gcagcagcgt ccacagagag gcgcgatgg catcctgcag       60
tatccgcacc ttttcttcgc ggcgctggcg ctggccctgc tcctcaccga cccgttccac      120
ctcggcccgc tcgccggggt ggactaccgg ccggtgaggc acgagctggc gccgtaccgc      180
gaggtgatgg cgcggtggcc gcgggacaac ggcagccggc tcaggcacgg caggctggag      240
ttcgtcggag aggtgttcgg gccggagtcc atcgagttcg accgcacgg ccgcggcccc       300
tacgccggcc tcgccgacgg ccgcgtcgtg cggtggatgg gggaggacgc cgggtgggag      360
acgttcgccg tcatgagccc tgactggtcg gagaaagttt gtgccaatgg ggtggagtcg      420
acgacgaaga agcagcacga gatggagcga cggtgcggcc ggcctctcgg gctgaggttt      480
cacggcgaga ccggcgagct ctacgtcgcc gacgcgtact acgggctcat gtccgtcggt      540
ccgaacggcg gggtggcgac ctctctcgcg agagaagtcg gcgggagccc ggtcaacttc      600
gcgaacgacc tcgacatcca ccgcaacggc tccgtgttct tcaccgacac gagcacgaga      660
tacaacagaa aggatcatct gaacgttctg ctagaaggtg aaggcacagg gaggctgctc      720
agatatgacc cagaaaccaa agctgcccat gtcgtgctga gcgggctggt cttcccgaat      780
ggcgtgcaga tttctgacga ccagcagttc ctcctcttct ccgaaacaac aaactgcagg      840
ataatgcggt actggctgga agggccaaga gccgggcagg tggaggtgtt cgccgacctg      900
ccggggttcc cggacaacgt gcgactgagc agcggcggcg gcggcggacg gttctgggtg      960
gcgatcgact gctgcaggac ggcggcgcag gaggtgttcg ccaagcggcc gtggctgcga     1020
acgctctact tcaagctgcc cctgacgatg cggacgctgg ggaagatggt cagcatgcgg     1080
atgcacaccc tcgtcgcgct cctcgacggc aaggggacg tcgtcgaggt gctcgaggac     1140
cggggcggcg aggtgatgcg gctggtgagc gaggtgaggg aggtggggcg caagctgtgg     1200
atcggcaccg tggctcataa ccacatcgcc acgatccctt acccgttgga agagcagagt     1260
agcagcaacg tgcttggtga ttga                                           1284

<210> SEQ ID NO 6
<211> LENGTH: 427
<212> TYPE: PRT
<213> ORGANISM: Oryza sativa

<400> SEQUENCE: 6
```

```
Met Glu Glu Lys Lys Gln Gln Gln Arg Pro Gln Arg Gly Arg Asp
1               5                   10                  15

Gly Ile Leu Gln Tyr Pro His Leu Phe Phe Ala Ala Leu Ala Leu Ala
                20              25                  30

Leu Leu Leu Thr Asp Pro Phe His Leu Gly Pro Leu Ala Gly Val Asp
            35              40                  45

Tyr Arg Pro Val Arg His Glu Leu Ala Pro Tyr Arg Glu Val Met Ala
        50              55                  60

Arg Trp Pro Arg Asp Asn Gly Ser Arg Leu Arg His Gly Arg Leu Glu
65                      70                  75                  80

Phe Val Gly Glu Val Phe Gly Pro Glu Ser Ile Glu Phe Asp Arg His
                85                  90                  95

Gly Arg Gly Pro Tyr Ala Gly Leu Ala Asp Gly Arg Val Val Arg Trp
                100                 105                 110

Met Gly Glu Asp Ala Gly Trp Glu Thr Phe Ala Val Met Ser Pro Asp
            115                 120                 125

Trp Ser Glu Lys Val Cys Ala Asn Gly Val Glu Ser Thr Thr Lys Lys
        130                 135                 140

Gln His Glu Met Glu Arg Arg Cys Gly Arg Pro Leu Gly Leu Arg Phe
145                 150                 155                 160

His Gly Glu Thr Gly Glu Leu Tyr Val Ala Asp Ala Tyr Tyr Gly Leu
                165                 170                 175

Met Ser Val Gly Pro Asn Gly Gly Val Ala Thr Ser Leu Ala Arg Glu
            180                 185                 190

Val Gly Gly Ser Pro Val Asn Phe Ala Asn Asp Leu Asp Ile His Arg
        195                 200                 205

Asn Gly Ser Val Phe Phe Thr Asp Thr Ser Thr Arg Tyr Asn Arg Lys
210                 215                 220

Asp His Leu Asn Val Leu Glu Gly Glu Gly Thr Gly Arg Leu Leu
225                 230                 235                 240

Arg Tyr Asp Pro Glu Thr Lys Ala Ala His Val Val Leu Ser Gly Leu
                245                 250                 255

Val Phe Pro Asn Gly Val Gln Ile Ser Asp Asp Gln Gln Phe Leu Leu
            260                 265                 270

Phe Ser Glu Thr Thr Asn Cys Arg Ile Met Arg Tyr Trp Leu Glu Gly
        275                 280                 285

Pro Arg Ala Gly Gln Val Glu Val Phe Ala Asp Leu Pro Gly Phe Pro
290                 295                 300

Asp Asn Val Arg Leu Ser Ser Gly Gly Gly Gly Arg Phe Trp Val
305                 310                 315                 320

Ala Ile Asp Cys Cys Arg Thr Ala Ala Gln Glu Val Phe Ala Lys Arg
                325                 330                 335

Pro Trp Leu Arg Thr Leu Tyr Phe Lys Leu Pro Leu Thr Met Arg Thr
            340                 345                 350

Leu Gly Lys Met Val Ser Met Arg Met His Thr Leu Val Ala Leu Leu
        355                 360                 365

Asp Gly Glu Gly Asp Val Val Glu Val Leu Glu Asp Arg Gly Gly Glu
370                 375                 380

Val Met Arg Leu Val Ser Glu Val Arg Glu Val Gly Arg Lys Leu Trp
385                 390                 395                 400

Ile Gly Thr Val Ala His Asn His Ile Ala Thr Ile Pro Tyr Pro Leu
                405                 410                 415
```

Glu Glu Gln Ser Ser Ser Asn Val Leu Gly Asp
            420                 425

<210> SEQ ID NO 7
<211> LENGTH: 534
<212> TYPE: DNA
<213> ORGANISM: Oryza sativa

<400> SEQUENCE: 7

| | | | | | |
|---|---|---|---|---|---|
| aatgcaaatc | agtgacaaca | actaactaag | atgacctcac | agcaattagg ctactgctgg | 60 |
| gtcctcctaa | ttgccttgct | atcgtgcagc | gcagccactg | ccagcgaggt cccggcgatc | 120 |
| atcgtgttcg | gggactcgac | ggtcgacgcc | ggcaacaaca | actacatcct caccgtcgcc | 180 |
| aagggcaatt | tcccgcctta | tggtcgcgac | ttcgacggcg | gcgtcgccac cggccgcttc | 240 |
| tccaatggcc | gccttgtcac | cgacttcgtg | tcggaggcgc | tggggctgcc gtcctctgtg | 300 |
| ccggcctatc | tcgactccac | ctacaccatt | gatcagcttg | ctactggtgt cagctttgct | 360 |
| tcaggcggca | ccgggctcga | tagtctcact | gccagagttg | tagtaagtta actcatctcc | 420 |
| caatatataa | ccttgcactt | gtctttttt | taaggaaagc | ggcaagagta ttgccgaata | 480 |
| tattagagga | aaagaaaatt | acggtttaca | tgttggtgat | tatacgatca aagc | 534 |

<210> SEQ ID NO 8
<211> LENGTH: 381
<212> TYPE: DNA
<213> ORGANISM: Oryza sativa

<400> SEQUENCE: 8

| | | | | | |
|---|---|---|---|---|---|
| atgacctcac | agcaattagg | ctactgctgg | gtcctcctaa | ttgccttgct atcgtgcagc | 60 |
| gcagccactg | ccagcgaggt | cccggcgatc | atcgtgttcg | gggactcgac ggtcgacgcc | 120 |
| ggcaacaaca | actacatcct | caccgtcgcc | aagggcaatt | tcccgcctta tggtcgcgac | 180 |
| ttcgacggcg | gcgtcgccac | cggccgcttc | tccaatggcc | gccttgtcac cgacttcgtg | 240 |
| tcggaggcgc | tggggctgcc | gtcctctgtg | ccggcctatc | tcgactccac ctacaccatt | 300 |
| gatcagcttg | ctactggtgt | cagctttgct | tcaggcggca | ccgggctcga tagtctcact | 360 |
| gccagagttg | tagtaagtta | a | | | 381 |

<210> SEQ ID NO 9
<211> LENGTH: 126
<212> TYPE: PRT
<213> ORGANISM: Oryza sativa

<400> SEQUENCE: 9

Met Thr Ser Gln Gln Leu Gly Tyr Cys Trp Val Leu Leu Ile Ala Leu
1               5                   10                  15

Leu Ser Cys Ser Ala Ala Thr Ala Ser Glu Val Pro Ala Ile Ile Val
            20                  25                  30

Phe Gly Asp Ser Thr Val Asp Ala Gly Asn Asn Asn Tyr Ile Leu Thr
        35                  40                  45

Val Ala Lys Gly Asn Phe Pro Pro Tyr Gly Arg Asp Phe Asp Gly Gly
    50                  55                  60

Val Ala Thr Gly Arg Phe Ser Asn Gly Arg Leu Val Thr Asp Phe Val
65                  70                  75                  80

Ser Glu Ala Leu Gly Leu Pro Ser Ser Val Pro Ala Tyr Leu Asp Ser
                85                  90                  95

Thr Tyr Thr Ile Asp Gln Leu Ala Thr Gly Val Ser Phe Ala Ser Gly
            100                 105                 110

Gly Thr Gly Leu Asp Ser Leu Thr Ala Arg Val Val Ser
        115                 120                 125

<210> SEQ ID NO 10
<211> LENGTH: 238
<212> TYPE: DNA
<213> ORGANISM: Oryza sativa

<400> SEQUENCE: 10
cggatagaca atggcgtata atcgcaatg gatggacgtg acgtgcagg gccgtgctcg     60 ccggccgtgt gaagggatga ggatagggac gcgcggtcgc atggctggga tggctgcctg   120
cgacaaggcc ggcggagagg ggaaatgtga ggaggcgatg agaggagagc gaggcggcgg   180 cggagggga gactggagaa gagaaggggg agcagttcag gggtagggtt ttgtggtg     238

<210> SEQ ID NO 11
<211> LENGTH: 216
<212> TYPE: DNA
<213> ORGANISM: Oryza sativa

<400> SEQUENCE: 11
atggcgtata atcgcaatg gatggacgtg acgtgcagg gccgtgctcg ccggccgtgt     60
gaagggatga ggatagggac gcgcggtcgc atggctggga tggctgcctg cgacaaggcc   120
ggcggagagg ggaaatgtga ggaggcgatg agaggagagc gaggcggcgg cggagggga   180 gactggagaa gagaaggggg agcagttcag gggtag                            216

<210> SEQ ID NO 12
<211> LENGTH: 71
<212> TYPE: PRT
<213> ORGANISM: Oryza sativa

<400> SEQUENCE: 12

Met Ala Tyr Lys Ser Gln Trp Met Asp Val Asp Val Gln Gly Arg Ala
1               5                   10                  15

Arg Arg Pro Cys Glu Gly Met Arg Ile Gly Thr Arg Gly Arg Met Ala
            20                  25                  30

Gly Met Ala Ala Cys Asp Lys Ala Gly Gly Glu Gly Lys Cys Glu Glu
        35                  40                  45

Ala Met Arg Gly Glu Arg Gly Gly Gly Gly Gly Asp Trp Arg Arg
    50                  55                  60

Glu Gly Gly Ala Val Gln Gly
65                  70

<210> SEQ ID NO 13
<211> LENGTH: 2685
<212> TYPE: DNA
<213> ORGANISM: Oryza sativa

<400> SEQUENCE: 13
gaatccttct ccatctccgg tcagcatagc tcccgctcgg ccgcgccgct catccctcac     60
tggcacaccg caccgtttct atcgcccgct gtcaccgctg agaagaggga cacaactgtc   120
gtgcgcggcc gagtggatgt ggtgtgaggc ggtgaggcg agggaacgcg gggagcttgg   180
ggcacggcgc ttcgagaccg ccgcccgggc gcgccgcacc gcctcactcg cactctccaa   240
ccgcaaggag ttcaccaccc cgcacaacgg cgccgtcaac tctctccagg tacacccccct   300 tctcactccc tcactcccct tctccttctc tcaccttagt ggtttagatc aatttgattt   360

-continued

```
gtacaccctg tagatggaat cttgcgtatt tggtgtgcaa ttcctgagtc gctcccgctg    420
gtgttttgta atttgacaat atggtcaggt tgatttgata gagcggcggt acctgctctc    480
gggcgcatcg gatggatcag ccgctatatt tgatgtgcag aatgcgatcg aatacgaagc    540
tgggttcatt gccaagcata ggagcattct ccttgtggac aagcagcatg aaaatggcca    600
caagttcgcg gtatctatgg ccgtatggta tcctgtggac actgggctgt tgtgacagc     660 ttcttttgat cagtatgtca agtgtggga tactaattcg actcaagtat gctttcatct     720
gctttgtcga ttgctaattt ttcttttgtc ttgcctcctt tgtggtggca atggtgtgat    780
cctgatgttc tgattttttg cctggttttc ttttctaggt cgtaatggat ttaagatgc     840 ctggaaaagt gtacagtgca gcaatgtccc caattgcaac aacacatatg ctgatcgcta    900
ctggaagtgc agatgttcag gtccgtttat gtgatattgc ttctggagcc tttacccaca    960
cgttgtctgg tcatcgtggt tagttgctta cttctagtgt agtgatgaaa atatgcttgc   1020
tttgtttgta tggttaccac cttatccttg gtatctgaca tgtcagatgg tatcatgtct   1080
ttggagtggt ctacttcaag tgagtggatt ttgatgagcg gtggttgtga tggagcaata   1140
cgatttgggg acataagacg agctggatgc tttcttgttc ttgatcaatc acggtctcaa   1200
ctaggaaggc ggcctccttt tcttgagggc acctcagata aggtatggtc accattatcc   1260
atcacttaca tttgttttca aaatatttgg ttgcaacgct aaagctggac ttccactttt   1320
attttctgca aaagcttcaa aaatgttgca gctttaagta aaacattatg gttgtaatgc   1380
tacagatcaa tactgtcagc cttcaagtaa aagctgattt ctgcggctat taatttatag   1440
gtttgtctca catattagtg tcagtatata ggtgctatgg atcagtttag tgctccaatt   1500
cttacaatat aaggtctgca tacattgttt cttgttgatt gttgtgccct agaaatgacg   1560
cgcaaactca ttgatctagt tgtgcaaatg atcaatgtat tcattttta ttttgactag    1620 gatcctttga actctttaca accttcatct tcttcaaaga tttactctgc acagcagagg   1680
acaggcaaga gtaagaaaca gtcacacaaa ttgcacaaaa gtcaaatccc tggacatgga   1740
catatccaac agagattgca ccctggtttg tcttctagtc aaaatcgtgc aacggcgcat   1800
tatggtgctg ttacgggatt aagaacaact acagatggga tgtaccttct tagctcaggt   1860
tgattgaatt taattgctat ttctatgagc attcgattgc tattgcttga aaggaattat   1920
tgcctatggc tatcttcttg ttatgcctgt atgcagtatg cattaatgat tgttatcctc   1980
tctcttcagg ttctgattct cgcttaagac tttgggatat tgattcaggc tgtaatactt   2040
tggtcaattt tgaagctatg cgattacaga ctagcaaacc actacaatta gctgtcactg   2100
aggatccatc acttgtattc atcccatgca tggcaagcat taaggtgtgg tcattttta    2160 gcttctcagt ttggacgctg aatttatac ttcaccttgt gttgccaaat tcatgtaggc    2220
gtacaattta tggtctggta tgacatttca acattccgt gggcactatg aacctgttaa    2280
ttgctgctac tatagtgcac aagaacaagt aagtcttccc tctactccta tcctctgtta   2340
accctgaatg ttcccgcatc aataccattg ctgagtcttt tggaattcag gagctttata   2400
ctggcagcaa tgacaggcaa attcttgtgt ggtctccatc aactccagca tttactgaaa   2460
tggtatattt tctatttctt gttatcatat atctttctgt agaattttcc tacatcctat   2520
caaattcaaa tttctcagga gtagtcgggc atattgggat attattgcat aagctttttt   2580
aggcatttga ttgttagcac tgctaaacct ctgcaggaag atgatggcaa gaggcaaatg   2640
gattttgtag tcgatgagga taactggagc gactgagaat tatgc                   2685
```

<210> SEQ ID NO 14
<211> LENGTH: 1116
<212> TYPE: DNA
<213> ORGANISM: Oryza sativa

<400> SEQUENCE: 14

```
atgtggtgtg aggcggtgag gcggagggaa cgcggggagc ttggggcacg gcgcttcgag      60
accgccgccc gggcgcgccg caccgcctca ctcgcactct ccaaccgcaa ggagttcacc     120
accccgcaca acggcgccgt caactctctc caggttgatt tgatagagcg gcggtacctg     180
ctctcgggcg catcggatgg atcagccgct atatttgatg tgcagaatgc gatcgaatac     240
gaagctgggt tcattgccaa gcataggagc attctccttg tggacaagca gcatgaaaat     300
ggccacaagt tcgcggtatc tatggccgta tggtatcctg tggacactgg gctgtttgtg     360
acagcttctt ttgatcagta tgtcaaagtg tgggatacta attcgactca agtcgtaatg     420
gattttaaga tgcctggaaa agtgtacagt gcagcaatgt ccccaattgc aacaacacat     480
atgctgatcg ctactggaag tgcagatgtt cagtggtcta cttcaagtga gtggattttg     540
atgagcggtg gttgtgatgg agcaatacga ttttgggaca taagacgagc tggatgcttt     600
cttgttcttg atcaatcacg gtctcaacta ggaaggcggc ctccttttct tgagggcacc     660
tcagataagg atcctttgaa ctctttacaa ccttcatctt cttcaaagat ttactctgca     720
cagcagagga caggcaagag ttctgattct cgcttaagac tttgggatat tgattcaggc     780
tgtaatactt tggtcaattt tgaagctatg cgattacaga ctagcaaacc actacaatta     840
gctgtcactg aggatccatc acttgtattc atcccatgca tggcaagcat taaggcgtac     900
aatttatggt ctggtatgac atttcaaaca ttccgtgggc actatgaacc tgttaattgc     960
tgctactata gtgcacaaga acaagagctt tatactggca gcaatgacag gcaaattctt    1020
gtgtggtctc catcaactcc agcatttact gaaatggaag atgatggcaa gaggcaaatg    1080
gattttgtag tcgatgagga taactggagc gactga                              1116
```

<210> SEQ ID NO 15
<211> LENGTH: 371
<212> TYPE: PRT
<213> ORGANISM: Oryza sativa

<400> SEQUENCE: 15

```
Met Trp Cys Glu Ala Val Arg Arg Arg Glu Arg Gly Glu Leu Gly Ala
1               5                   10                  15

Arg Arg Phe Glu Thr Ala Ala Arg Ala Arg Arg Thr Ala Ser Leu Ala
            20                  25                  30

Leu Ser Asn Arg Lys Glu Phe Thr Thr Pro His Asn Gly Ala Val Asn
        35                  40                  45

Ser Leu Gln Val Asp Leu Ile Glu Arg Arg Tyr Leu Leu Ser Gly Ala
    50                  55                  60

Ser Asp Gly Ser Ala Ala Ile Phe Asp Val Gln Asn Ala Ile Glu Tyr
65                  70                  75                  80

Glu Ala Gly Phe Ile Ala Lys His Arg Ser Ile Leu Leu Val Asp Lys
                85                  90                  95

Gln His Glu Asn Gly His Lys Phe Ala Val Ser Met Ala Val Trp Tyr
            100                 105                 110

Pro Val Asp Thr Gly Leu Phe Val Thr Ala Ser Phe Asp Gln Tyr Val
        115                 120                 125

Lys Val Trp Asp Thr Asn Ser Thr Gln Val Val Met Asp Phe Lys Met
    130                 135                 140
```

```
Pro Gly Lys Val Tyr Ser Ala Ala Met Ser Pro Ile Ala Thr Thr His
145                 150                 155                 160

Met Leu Ile Ala Thr Gly Ser Ala Asp Val Gln Trp Ser Thr Ser Ser
            165                 170                 175

Glu Trp Ile Leu Met Ser Gly Cys Asp Gly Ala Ile Arg Phe Trp
        180                 185                 190

Asp Ile Arg Arg Ala Gly Cys Phe Leu Val Leu Asp Gln Ser Arg Ser
            195                 200                 205

Gln Leu Gly Arg Arg Pro Pro Phe Leu Glu Gly Thr Ser Asp Lys Asp
    210                 215                 220

Pro Leu Asn Ser Leu Gln Pro Ser Ser Ser Lys Ile Tyr Ser Ala
225                 230                 235                 240

Gln Gln Arg Thr Gly Lys Ser Ser Asp Ser Arg Leu Arg Leu Trp Asp
            245                 250                 255

Ile Asp Ser Gly Cys Asn Thr Leu Val Asn Phe Glu Ala Met Arg Leu
            260                 265                 270

Gln Thr Ser Lys Pro Leu Gln Leu Ala Val Thr Glu Asp Pro Ser Leu
            275                 280                 285

Val Phe Ile Pro Cys Met Ala Ser Ile Lys Ala Tyr Asn Leu Trp Ser
    290                 295                 300

Gly Met Thr Phe Gln Thr Phe Arg Gly His Tyr Glu Pro Val Asn Cys
305                 310                 315                 320

Cys Tyr Tyr Ser Ala Gln Glu Gln Leu Tyr Thr Gly Ser Asn Asp
            325                 330                 335

Arg Gln Ile Leu Val Trp Ser Pro Ser Thr Pro Ala Phe Thr Glu Met
            340                 345                 350

Glu Asp Asp Gly Lys Arg Gln Met Asp Phe Val Val Asp Glu Asp Asn
            355                 360                 365

Trp Ser Asp
    370

<210> SEQ ID NO 16
<211> LENGTH: 5476
<212> TYPE: DNA
<213> ORGANISM: Oryza sativa

<400> SEQUENCE: 16
gacatgtcgt ggcagagctc agtgtcctgg cagccggaca cgtcgtgggc gcagccccac      60
ggcctcggcg ccgccgtcgg gccctgggcg cccgccagga tggggagcgc cggccgccgt     120
ggccccgcgc tgttccggcg gacggcgagg gagtactacg tgtcgaggcg gtccgcccgc     180
ccgcgctacc gcgacgtctc ctcgtcggcg cacaggcccg tcgccgccgc cgccggcggc     240
ggtggcggca ggcggctgga gctgcagagc gtggtgaccg acgcgagccg cgccatcgtc     300
gtggtgccga cacctccttc gccagcaac gacgacagcg tcgtcgtcgc cgactccgcc     360
gtctactccg cgcccggcca tgacgccggc cgaggaggac gagccatggt gaggtacagc     420
gacaccaacg ccgccgccgc cgcctcccgc gaggtctcct tctcgcgcga caaccacgac     480
cagctctacg tctccgcggc gcggcgtgac ccgcccagct tcggctacga catcagcgtc     540
gcgtccttca gcggccagag ccggtacgag gacgccgtcg gcgactacga cgacgacgac     600
gacgagatcg acgtgagggt cgggaagccc gtcggcgtcg cggggctttt caagtactcg     660
acggccatgg acatcgtcct cctcgtgctc gggtgcgtcg gcgccatgat caacggcggc     720
tcgctgccat ggtactccta cctgttcggt aacttcgtca acaagatcgt caacgtcgac     780
```

```
aagacgcaga tgatgaagga cgtcaagcag gtctcgccgc gtgcatcgcc atgatcattt    840
cttcgatttc tcagcttcga ttcaaatccg atcttctcat cttcgtttct tgttcgatgc    900
cagattagtg tgtacatggc gttccttgct gcagttgtcg tcgtaggagc ctatcttggt    960
gagcattttt gcaaattaat catgaaaaag ttcaattcct gggaatctct tgaatcgaat   1020
tatgagtttc taattatgtg cgatcagaga tcacctgctg gaggatcatc ggcgagaggt   1080
cggcgctgcg gatgcggcga gagtacctga aggcggtgct gaggcaggag atcggattct   1140
tcgacacgga ggtgagcacc ggcgaggtga tgcacagcat ctccggcgat gtcgcccaaa   1200
tccaagaagt catgggagag aaggtagagc gcacacacaa aatttacccc caaacacata   1260
tgttcaaaag ctgacacatg actaaaatct tgtgcacatt ttgtaaagat tccaggattc   1320
gtgcaccacg tcttcacctt cgtcttcggc tacgtggtcg gcttcgccaa atcgtggagg   1380
atcgctctcg ccgtcttcgc cgtcacgcct gccatgatgg cgtgcggcat ggcctacaag   1440
gccatctatg gcggcctcac cgccaaggaa gaggtttagc agccggccac tcactctctc   1500
gctcttatac tgaaaccaaa tttgatgaat tgaaagtttg aaaccaattt gatggaattt   1560
ggtaggcatc gtaccagcgt gccggcgacg tggcgcagca ggcgatcagc tcgatcagga   1620
cggtgatgtc gttcgtcatg gaggagcggc tcgccggcga gtacgccgag tggctggaca   1680
aggcggcgcc gatcggcgtc aagatggggt tcgccaaggg cgccggcatg ggggtgatct   1740
acctggtgac ctactcccag tgggcgctgg cgctctggta cggctccagg ctcgtcgcca   1800
acggcgagat caagggcggc gacgccatcg cctgcttctt cggcgtcatg gtcggaggaa   1860
ggcacgcaca tcaacctcct cgcaccgctt cttgttgtcg tcaatggcgc cggtcgccgg   1920
agtttcgtgg ttggtgtggt ggtgatctct gatctcggaa tggttgtgtg tgtgtgcagg   1980
ggcttggcgc tgacgctgtc gtacatggcg cagttcgcgc agggcacggt ggcggcgggg   2040
cgggtgttcg aggtcatcga ccgggtgccg gagatcgacg cgtacggcgc cggcgggcgg   2100
gcgctgccgg cggtgaaggg gcggatggag ttcaaggacg tggagttcgc gtacccgtcg   2160
cggccggacg ccatggtgct gtacaacctc aacctggtca tccccgccgc caagacgctg   2220
gcgctcgtcg gcgtcagcgg cggcggcaag tccaccatgt tcgcgctcat cgagcgcttc   2280
tacgacccga ctcgaggtga gagggaatgg ccattgacgc gcacgcagag cacgaccatg   2340
gcgagatcgt cggtgatcga tgacgaagct tttgcgtccg tggggtgtgc agggtcgatc   2400
acgttggacg gccatgacct cgcgtcgctg aacctccggt ggctccggtc gcagatcggg   2460
ctcgtcgggc aggagcccgt cctcttctcc acctccatca tcgagaacgt catgatgggg   2520
aaggagaacg ccacgcgcca cgacgccatc tcggcgtgcg ccatggccaa cgtccacacc   2580
ttcgtcctcg ccctccccga cggctacgac actcaggtca cactgacaca cacaaactaa   2640
tcaaccatta atctcacgga ttatctgtta attaatcata gataatataa tatgtgtgtt   2700
aattaggttg gggaccgtgg ggcccagctg tcgggggac agaagcagcg gatcgcgctg   2760
gcgcgcgcca tcatccgcga cccgcgcatc ctgctgctgg acgagccaac cagcgcgctg   2820
gacacccagt cggaggccgt ggtgcagcag tccatcgacc gcctcgccgc cggccgcacc   2880
gtcgtcgtca tcgcgcaccg cctcgccacc gtccgcaacg ccgacaccat cgcggtgctc   2940
gaccgcggcg ccgtcgtcga gtccggccgc cacgccgacc tcatggcccg ccgcgggccc   3000
tactccgcgc tggtcagcct cgcctccgac agcggcggcg ccaggccaga cctcgccggc   3060
gctgcagcgg cgtacaccag cttcaccgac gagtcggggt acgacgtgtc ggtgtccaag   3120
```

```
tcgaggtacg gcttccagac gattcgagaa gaggaggaga agaaggattc gcaggacgcc    3180
aaggtgaggg tctccgagat atggaggctg cagcggcggg aaggtccatt gctgattttg    3240
gggttcttga tgggcataca cgccggcgcg gtgttctcgg tgttcccgct gctgctgggc    3300
caggcggtgg aggtgtactt cgacgccgac acggcgagga tgaagcggca ggtggagtac    3360
ctggccatgg cggtggtcgg cctcggcgtg gcctgcatcc tgaccatgac ggggcagcag    3420
gggctgtgcg gctgggcggg cgcccggctc accatgcgcg tccggaccgg cctcttccgc    3480
gccatcatgc ggcaggagcc cgcgtggttc gacgaggagg acaacgcgat gggcgtcctg    3540
gtgacgcggc tcgcgcggga cgccgtcgcg ttccgctcca tgttcggcga ccgctacgcc    3600
gtgctgctca tggccgtcgg ctcggccggc gtggggctcg gcatttgctt cgggctggac    3660
tggcggctca cgctggtggc cacggcgtgc acgccgctga cgctcggcgc cagctacctc    3720
aacctgctca tcaacgtggg cgccaggtcc gacgacggcg cgtacgcccg cgccagcggc    3780
atcgccgccg cgccgtgtc gaacgtgcgc accgtcgcgg cgctctgcgc ccagggcagc    3840
gtcgtcggca cgttcaaccg cgcgctgac gggccggcgg ccaaggccag ccggagatcg    3900
cagctcatgg gcgtcatcct cgggctctcc cagggcgcca tgtacggcgc ctacacggcg    3960
acgctctgcc ccggcgccca cttcatcaac aatggcgtgt ccaccttcgg cgacgtgtcc    4020
aagatcttcc tcatcctcgt cctcagctcc ttctccgtcg ccagctcgc cggcctcgcc    4080
cctgacacct ccggcgcccc ggcggccatc gccggcatac taaccatcct caagcgacgt    4140
ccggcgatca ccggagactc caccaagcga aggatcacga tcaaggacgg gaagcccatc    4200
gacgtggagc tccggaaggt gacgttcgcg tacccgtcgc ggccggaggt gacggtgctg    4260
agcggcttct cgctgcgggt gaaggccggc acgacggtgg cggtggtcgg cgcgagcggg    4320
agcgggaagt cgacggtggt gtggctggtg cagcggttct acgacccggg cgacgggaag    4380
gtggtggtcg gcggcgtgga cgcgcgggag cttgacctca gtggctccg cggcgagtgc    4440
gccatggtgg gccaggagcc ggccctcttc agcgggtcca tccgagacaa catcgggttc    4500
ggcaacccaa aggcctcgtg ggccgaaatc gaggaggccg ccaaggaggc caacatccac    4560
aagttcatct ccgccctccc ccaaggctac gaaacccagg ttaactacta aaaatttcaa    4620
atctaagcat tcaaatatct tcataaatta tagagtacat tccataaaac atccaagtta    4680
cgtaaaaaaa taaattatcc aagttatata aaaccgtaaa tattttgaca cgtgacacat    4740
aaccctaaat actatggtac taatatttga taaaaccaca ccgttaacca tttctgatac    4800
aatcctatat caaaatttta aaatgcaggt gtaacattta tatgatggat agaatccTta    4860
taaaattgat atgtgattgt agaattaaat agtgtggttt tgtgaaactt aatcatgata    4920
cgtgaagttc tatgccatat gccaaaatct atgaagtttt gtgtaatttg gaccataata    4980
cgtgtggttt gtaaaattta ctctaaacta ccattttgaa atgattattg ggtgaatttc    5040
agttgaattg ttgaactaaa atttctttgt tttgcttagg ttggggagag tggggtgcag    5100
ttgtcaggtg ggcagaagca gaggatcgcg atcgcgcggg cgatcgtgaa gcaggcgagg    5160
atactgctgc tggacgaggc gagcagcgcg ctggacctgg agtccgagcg gcacgtgcag    5220
gaggcccctga ggagggcctc gcggcgcgcc acggcgatca ccgtggcgca ccgcctctcc    5280
accgtgcgcg acgccgaccg catcgccgtc gtcagcgccg gcagggtcgt cgagttcggc    5340
ggccatgacg ccctcctcgc cggccacggc gacggcctct acgctgccat ggtgaaggcg    5400
gagacggagg cacaagcgtt caagtaaaaa aaaaaaaaag gttatctcgt tgctggggga    5460
tttgcaatta taacac                                                   5476
```

<210> SEQ ID NO 17
<211> LENGTH: 4449
<212> TYPE: DNA
<213> ORGANISM: Oryza sativa

<400> SEQUENCE: 17

| | | | | | | |
|---|---|---|---|---|---|---|
| atgtcgtggc | agagctcagt | gtcctggcag | ccggacacgt | cgtgggcgca | gccccacggc | 60 |
| ctcggcgccg | ccgtcgggcc | ctgggcgccc | gccaggatgg | ggagcgccgg | ccgccgtggc | 120 |
| cccgcgctgt | tccggcggac | ggcgagggag | tactacgtgt | cgaggcggtc | cgcccgcccg | 180 |
| cgctaccgcg | acgtctcctc | gtcggcgcac | aggcccgtcg | ccgccgccgc | cggcggcggt | 240 |
| ggcggcaggc | ggctggagct | gcagagcgtg | gtgaccgacg | cgagccgcgc | catcgtcgtg | 300 |
| gtgccgaaca | cctccttcgc | cagcaacgac | gacagcgtcg | tcgtcgccga | ctccgccgtc | 360 |
| tactccgcgc | ccggccatga | cgccggccga | ggaggacgag | ccatggtgag | gtacagcgac | 420 |
| accaacgccg | ccgccgccgc | ctcccgcgag | gtctccttct | cgcgcgacaa | ccacgaccag | 480 |
| ctctacgtct | ccgcggcgcg | gcgtgacccg | cccagcttcg | gctacgacat | cagcgtcgcg | 540 |
| tccttcagcg | ccagagccg | gtacgaggac | gccgtcggcg | actacgacga | cgacgacgac | 600 |
| gagatcgacg | tgagggtcgg | gaagcccgtc | ggcgtcgcgg | ggcttttcaa | gtactcgacg | 660 |
| gccatggaca | tcgtcctcct | cgtgctcggg | tgcgtcggcg | ccatgatcaa | cggcggctcg | 720 |
| ctgccatggt | actcctacct | gttcggtaac | ttcgtcaaca | gatcgtcaa | cgtcgacaag | 780 |
| acgcagatga | tgaaggacgt | caagcagatt | agtgtgtaca | tggcgttcct | tgctgcagtt | 840 |
| gtcgtcgtag | gagcctatct | tgagatcacc | tgctggagga | tcatcggcga | gaggtcggcg | 900 |
| ctgcggatgc | ggcgagagta | cctgaaggcg | gtgctgaggc | aggagatcgg | attcttcgac | 960 |
| acggaggtga | gcaccggcga | ggtgatgcac | agcatctccg | gcgatgtcgc | ccaaatccaa | 1020 |
| gaagtcatgg | gagagaagat | tccaggattc | gtgcaccacg | tcttcacctt | cgtcttcggc | 1080 |
| tacgtggtcg | gcttcgccaa | atcgtggagg | atcgctctcg | ccgtcttcgc | cgtcacgcct | 1140 |
| gccatgatgg | cgtgcggcat | ggcctacaag | gccatctatg | cggcctcac | cgccaaggaa | 1200 |
| gaggcatcgt | accagcgtgc | cggcgacgtg | gcgcagcagg | cgatcagctc | gatcaggacg | 1260 |
| gtgatgtcgt | tcgtcatgga | ggagcggctc | gccggcgagt | acgccgagtg | gctggacaag | 1320 |
| gcggcgccga | tcgcgtcaa | gatggggttc | gccaagggcg | ccggcatggg | ggtgatctac | 1380 |
| ctggtgacct | actcccagtg | ggcgctggcg | ctctggtacg | gctccaggct | cgtcgccaac | 1440 |
| ggcgagatca | agggcggcga | cgccatcgcc | tgcttcttcg | gcgtcatggt | cggaggaagg | 1500 |
| cacgcacatc | aacctcctcg | caccgcttct | tgttgtcgtc | aatggcgccg | gtcgccggag | 1560 |
| tttcgtggtt | ggggcttggc | gctgacgctg | tcgtacatgg | cgcagttcgc | gcagggcacg | 1620 |
| gtggcggcgg | ggcgggtgtt | cgaggtcatc | gaccgggtgc | cggagatcga | cgcgtacggc | 1680 |
| gccgcgggc | gggcgctgcc | ggcggtgaag | gggcggatgg | agttcaagga | cgtggagttc | 1740 |
| gcgtacccgt | cgcggccgga | cgccatggtg | ctgtacaacc | tcaacctggt | catccccgcc | 1800 |
| gccaagacgc | tggcgctcgt | cggcgtcagc | ggcggcggca | agtccaccat | gttcgcgctc | 1860 |
| atcgagcgct | tctacgaccc | gactcgaggt | gagagggaat | ggccattgac | gcgcacgcag | 1920 |
| agcacgacca | tggcgagatc | gtcggtgatc | gatgacgaag | cttttgcgtc | cgtggggtgt | 1980 |
| gcagggtcga | tcacgttgga | cggccatgac | ctcgcgtcgc | tgaacctccg | gtggctccgg | 2040 |
| tcgcagatcg | ggctcgtcgg | gcaggagccc | gtcctcttct | ccacctccat | catcgagaac | 2100 |

```
gtcatgatgg ggaaggagaa cgccacgcgc cacgacgcca tctcggcgtg cgccatggcc   2160
aacgtccaca ccttcgtcct cgccctcccc gacggctacg acactcaggt tggggaccgt   2220
ggggcccagc tgtcgggggg acagaagcag cggatcgcgc tggcgcgcgc catcatccgc   2280
gacccgcgca tcctgctgct ggacgagcca accagcgcgc tggacaccca gtcggaggcc   2340
gtggtgcagc agtccatcga ccgcctcgcc gccggccgca ccgtcgtcgt catcgcgcac   2400
cgcctcgcca ccgtccgcaa cgccgacacc atcgcggtgc tcgaccgcgg cgccgtcgtc   2460
gagtccggcc gccacgccga cctcatggcc cgccgcgggc cctactccgc gctggtcagc   2520
ctcgcctccg acagcggcgg cgccaggcca gacctcgccg cgcgctgcagc ggcgtacacc   2580 agcttcaccg acgagtcggg gtacgacgtg tcggtgtcca agtcgaggta cggcttccag   2640
acgattcgag aagaggagga gaagaaggat tcgcaggacg ccaaggtgag ggtctccgag   2700
atatggaggc tgcagcggcg ggaaggtcca ttgctgattt tggggttctt gatgggcata   2760
cacgccggcg cggtgttctc ggtgttcccg ctgctgctgg ccaggcggt ggaggtgtac   2820 ttcgacgccg acacggcgag gatgaagcgg caggtggagt acctgccat ggcggtggtc   2880 ggcctcggcg tggcctgcat cctgaccatg acggggcagc aggggctgtg cggctgggcg   2940
ggcgcccggc tcaccatgcg cgtccgggac cgcctcttcc gcgccatcat gcggcaggag   3000
cccgcgtggt tcgacgagga ggacaacgcg atgggcgtcc tggtgacgcg gctcgcgcgg   3060
gacgccgtcg cgttccgctc catgttcggc gaccgctacg ccgtgctgct catggccgtc   3120
ggctcggccg gcgtggggct cggcatttgc ttcgggctgg actggcggct cacgctggtg   3180
gccacgcgcg t gcacgccgct gacgctcggc gccagctacc tcaacctgct catcaacgtg   3240
ggcgccaggt ccgacgacgg cgcgtacgcc cgcgccagcg catcgccgc cggcgccgtg   3300 tcgaacgtgc gcaccgtcgc ggcgctctgc gcccagggca gcgtcgtcgg cacgttcaac   3360
cgcgcgctgg acgggccggc ggccaaggcc agccggagat cgcagctcat gggcgtcatc   3420
ctcgggctct cccagggcgc catgtacggc gcctacacgg cgacgctctg cgccggcgcc   3480
cacttcatca acaatggcgt gtccaccttc ggcgacgtgt ccaagatctt cctcatcctc   3540
gtcctcagct ccttctccgt cggccagctc gccggcctcg cccctgacac ctccggcgcc   3600
ccggcggcca tcgccggcat actaaccatc ctcaagcgac gtccggcgat caccggagac   3660
tccaccaagc gaaggatcac gatcaaggac gggaagccca tcgacgtgga gctccggaag   3720
gtgacgttcg cgtacccgtc gcggccggag gtgacggtgc tgagcggctt ctcgctgcgg   3780
gtgaaggccg gcacgacggt ggcggtggtc ggcgcgagcg ggagcgggaa gtcgacggtg   3840
gtgtggctgg tgcagcggtt ctacgacccg ggcgacggga aggtggtggt cggcggcgtg   3900
gacgcgcggg agcttgacct caagtggctc cgcggcgagt gcgccatggt gggccaggag   3960
ccggccctct tcagcgggtc catccgagac aacatcgggt tcggcaaccc aaaggcctcg   4020
tgggccgaaa tcgaggaggc cgccaaggag gccaacatcc acaagttcat ctccgccctc   4080
ccccaaggct acgaaaccca ggttggggag agtggggtgc agttgtcagg tgggcagaag   4140
cagaggatcg cgatcgcgcg ggcgatcgtg aagcaggcga ggatactgct gctggacgag   4200
gcgagcagcg cgctgaacct ggagtccgag cggcacgtgc aggaggccct gaggagggcc   4260
tcgcggcgcg ccacggcgat caccgtggcg caccgcctct ccaccgtgcg cgacgccgac   4320
cgcatcgccg tcgtcagcgc cggcagggtc gtcgagttcg gcggccatga cgccctcctc   4380 gccgccacg cgacggcct ctacgctgcc atggtgaagg cggagacgga ggcacaagcg   4440
ttcaagtaa                                                           4449
```

<210> SEQ ID NO 18
<211> LENGTH: 1482
<212> TYPE: PRT
<213> ORGANISM: Oryza sativa

<400> SEQUENCE: 18

```
Met Ser Trp Gln Ser Ser Val Ser Trp Gln Pro Asp Thr Ser Trp Ala
1               5                   10                  15

Gln Pro His Gly Leu Gly Ala Ala Val Gly Pro Trp Ala Pro Ala Arg
            20                  25                  30

Met Gly Ser Ala Gly Arg Arg Gly Pro Ala Leu Phe Arg Arg Thr Ala
        35                  40                  45

Arg Glu Tyr Tyr Val Ser Arg Ser Ala Arg Pro Arg Tyr Arg Asp
    50                  55                  60

Val Ser Ser Ser Ala His Arg Pro Val Ala Ala Ala Gly Gly Gly
65                  70                  75                  80

Gly Gly Arg Arg Leu Glu Leu Gln Ser Val Val Thr Asp Ala Ser Arg
                85                  90                  95

Ala Ile Val Val Val Pro Asn Thr Ser Phe Ala Ser Asn Asp Asp Ser
            100                 105                 110

Val Val Val Ala Asp Ser Ala Val Tyr Ser Ala Pro Gly His Asp Ala
        115                 120                 125

Gly Arg Gly Gly Arg Ala Met Val Arg Tyr Ser Asp Thr Asn Ala Ala
    130                 135                 140

Ala Ala Ala Ser Arg Glu Val Ser Phe Ser Arg Asp Asn His Asp Gln
145                 150                 155                 160

Leu Tyr Val Ser Ala Ala Arg Arg Asp Pro Pro Ser Phe Gly Tyr Asp
                165                 170                 175

Ile Ser Val Ala Ser Phe Ser Gly Gln Ser Arg Tyr Glu Asp Ala Val
            180                 185                 190

Gly Asp Tyr Asp Asp Asp Asp Glu Ile Asp Val Arg Val Gly Lys
        195                 200                 205

Pro Val Gly Val Ala Gly Leu Phe Lys Tyr Ser Thr Ala Met Asp Ile
    210                 215                 220

Val Leu Leu Val Leu Gly Cys Val Gly Ala Met Ile Asn Gly Gly Ser
225                 230                 235                 240

Leu Pro Trp Tyr Ser Tyr Leu Phe Gly Asn Phe Val Asn Lys Ile Val
                245                 250                 255

Asn Val Asp Lys Thr Gln Met Met Lys Asp Val Lys Gln Ile Ser Val
            260                 265                 270

Tyr Met Ala Phe Leu Ala Ala Val Val Val Gly Ala Tyr Leu Glu
        275                 280                 285

Ile Thr Cys Trp Arg Ile Ile Gly Glu Arg Ser Ala Leu Arg Met Arg
    290                 295                 300

Arg Glu Tyr Leu Lys Ala Val Leu Arg Gln Ile Gly Phe Phe Asp
305                 310                 315                 320

Thr Glu Val Ser Thr Gly Glu Val Met His Ser Ile Ser Gly Asp Val
                325                 330                 335

Ala Gln Ile Gln Glu Val Met Gly Glu Lys Ile Pro Gly Phe Val His
            340                 345                 350

His Val Phe Thr Phe Val Phe Gly Tyr Val Val Gly Phe Ala Lys Ser
        355                 360                 365

Trp Arg Ile Ala Leu Ala Val Phe Ala Val Thr Pro Ala Met Met Ala
```

```
            370                 375                 380
Cys Gly Met Ala Tyr Lys Ala Ile Tyr Gly Gly Leu Thr Ala Lys Glu
385                 390                 395                 400

Glu Ala Ser Tyr Gln Arg Ala Gly Asp Val Ala Gln Gln Ala Ile Ser
                405                 410                 415

Ser Ile Arg Thr Val Met Ser Phe Val Met Glu Arg Leu Ala Gly
                420                 425                 430

Glu Tyr Ala Glu Trp Leu Asp Lys Ala Ala Pro Ile Gly Val Lys Met
                435                 440                 445

Gly Phe Ala Lys Gly Ala Gly Met Gly Val Ile Tyr Leu Val Thr Tyr
450                 455                 460

Ser Gln Trp Ala Leu Ala Leu Trp Tyr Gly Ser Arg Leu Val Ala Asn
465                 470                 475                 480

Gly Glu Ile Lys Gly Gly Asp Ala Ile Ala Cys Phe Phe Gly Val Met
                485                 490                 495

Val Gly Gly Arg His Ala His Gln Pro Pro Arg Thr Ala Ser Cys Cys
                500                 505                 510

Arg Gln Trp Arg Arg Ser Pro Glu Phe Arg Gly Trp Gly Leu Ala Leu
                515                 520                 525

Thr Leu Ser Tyr Met Ala Gln Phe Ala Gln Gly Thr Val Ala Ala Gly
                530                 535                 540

Arg Val Phe Glu Val Ile Asp Arg Val Pro Glu Ile Asp Ala Tyr Gly
545                 550                 555                 560

Ala Gly Gly Arg Ala Leu Pro Ala Val Lys Gly Arg Met Glu Phe Lys
                565                 570                 575

Asp Val Glu Phe Ala Tyr Pro Ser Arg Pro Asp Ala Met Val Leu Tyr
                580                 585                 590

Asn Leu Asn Leu Val Ile Pro Ala Ala Lys Thr Leu Ala Leu Val Gly
                595                 600                 605

Val Ser Gly Gly Gly Lys Ser Thr Met Phe Ala Leu Ile Glu Arg Phe
610                 615                 620

Tyr Asp Pro Thr Arg Gly Glu Arg Glu Trp Pro Leu Thr Arg Thr Gln
625                 630                 635                 640

Ser Thr Thr Met Ala Arg Ser Ser Val Ile Asp Asp Glu Ala Phe Ala
                645                 650                 655

Ser Val Gly Cys Ala Gly Ser Ile Thr Leu Asp Gly His Asp Leu Ala
                660                 665                 670

Ser Leu Asn Leu Arg Trp Leu Arg Ser Gln Ile Gly Leu Val Gly Gln
                675                 680                 685

Glu Pro Val Leu Phe Ser Thr Ser Ile Ile Glu Asn Val Met Met Gly
                690                 695                 700

Lys Glu Asn Ala Thr Arg His Asp Ala Ile Ser Ala Cys Ala Met Ala
705                 710                 715                 720

Asn Val His Thr Phe Val Leu Ala Leu Pro Asp Gly Tyr Asp Thr Gln
                725                 730                 735

Val Gly Asp Arg Gly Ala Gln Leu Ser Gly Gly Gln Lys Gln Arg Ile
                740                 745                 750

Ala Leu Ala Arg Ala Ile Ile Arg Asp Pro Arg Ile Leu Leu Leu Asp
                755                 760                 765

Glu Pro Thr Ser Ala Leu Asp Thr Gln Ser Glu Ala Val Val Gln Gln
                770                 775                 780

Ser Ile Asp Arg Leu Ala Ala Gly Arg Thr Val Val Ile Ala His
785                 790                 795                 800
```

-continued

```
Arg Leu Ala Thr Val Arg Asn Ala Asp Thr Ile Ala Val Leu Asp Arg
            805                 810                 815

Gly Ala Val Val Glu Ser Gly Arg His Ala Asp Leu Met Ala Arg Arg
            820                 825                 830

Gly Pro Tyr Ser Ala Leu Val Ser Leu Ala Ser Asp Ser Gly Gly Ala
            835                 840                 845

Arg Pro Asp Leu Ala Gly Ala Ala Ala Tyr Thr Ser Phe Thr Asp
            850                 855                 860

Glu Ser Gly Tyr Asp Val Ser Val Ser Lys Ser Arg Tyr Gly Phe Gln
865                 870                 875                 880

Thr Ile Arg Glu Glu Glu Lys Lys Asp Ser Gln Asp Ala Lys Val
                885                 890                 895

Arg Val Ser Glu Ile Trp Arg Leu Gln Arg Arg Glu Gly Pro Leu Leu
                900                 905                 910

Ile Leu Gly Phe Leu Met Gly Ile His Ala Gly Ala Val Phe Ser Val
                915                 920                 925

Phe Pro Leu Leu Leu Gly Gln Ala Val Glu Val Tyr Phe Asp Ala Asp
            930                 935                 940

Thr Ala Arg Met Lys Arg Gln Val Glu Tyr Leu Ala Met Ala Val Val
945                 950                 955                 960

Gly Leu Gly Val Ala Cys Ile Leu Thr Met Thr Gly Gln Gln Gly Leu
                965                 970                 975

Cys Gly Trp Ala Gly Ala Arg Leu Thr Met Arg Val Arg Asp Arg Leu
                980                 985                 990

Phe Arg Ala Ile Met Arg Gln Glu  Pro Ala Trp Phe Asp  Glu Glu Asp
            995                 1000                1005

Asn Ala Met Gly Val Leu Val  Thr Arg Leu Ala Arg  Asp Ala Val
    1010                1015                1020

Ala Phe Arg Ser Met Phe Gly  Asp Arg Tyr Ala Val  Leu Leu Met
    1025                1030                1035

Ala Val Gly Ser Ala Gly Val  Gly Leu Gly Ile Cys  Phe Gly Leu
    1040                1045                1050

Asp Trp Arg Leu Thr Leu Val  Ala Thr Ala Cys Thr  Pro Leu Thr
    1055                1060                1065

Leu Gly Ala Ser Tyr Leu Asn  Leu Leu Ile Asn Val  Gly Ala Arg
    1070                1075                1080

Ser Asp Asp Gly Ala Tyr Ala  Arg Ala Ser Gly Ile  Ala Ala Gly
    1085                1090                1095

Ala Val Ser Asn Val Arg Thr  Val Ala Ala Leu Cys  Ala Gln Gly
    1100                1105                1110

Ser Val Val Gly Thr Phe Asn  Arg Ala Leu Asp Gly  Pro Ala Ala
    1115                1120                1125

Lys Ala Ser Arg Arg Ser Gln  Leu Met Gly Val Ile  Leu Gly Leu
    1130                1135                1140

Ser Gln Gly Ala Met Tyr Gly  Ala Tyr Thr Ala Thr  Leu Cys Ala
    1145                1150                1155

Gly Ala His Phe Ile Asn Asn  Gly Val Ser Thr Phe  Gly Asp Val
    1160                1165                1170

Ser Lys Ile Phe Leu Ile Leu  Val Leu Ser Ser Phe  Ser Val Gly
    1175                1180                1185

Gln Leu Ala Gly Leu Ala Pro  Asp Thr Ser Gly Ala  Pro Ala Ala
    1190                1195                1200
```

```
Ile Ala Gly Ile Leu Thr Ile Leu Lys Arg Arg Pro Ala Ile Thr
    1205                1210                1215

Gly Asp Ser Thr Lys Arg Arg Ile Thr Ile Lys Asp Gly Lys Pro
    1220                1225                1230

Ile Asp Val Glu Leu Arg Lys Val Thr Phe Ala Tyr Pro Ser Arg
    1235                1240                1245

Pro Glu Val Thr Val Leu Ser Gly Phe Ser Leu Arg Val Lys Ala
    1250                1255                1260

Gly Thr Thr Val Ala Val Val Gly Ala Ser Gly Ser Gly Lys Ser
    1265                1270                1275

Thr Val Val Trp Leu Val Gln Arg Phe Tyr Asp Pro Gly Asp Gly
    1280                1285                1290

Lys Val Val Gly Gly Val Asp Ala Arg Glu Leu Asp Leu Lys
    1295                1300                1305

Trp Leu Arg Gly Glu Cys Ala Met Val Gly Gln Glu Pro Ala Leu
    1310                1315                1320

Phe Ser Gly Ser Ile Arg Asp Asn Ile Gly Phe Gly Asn Pro Lys
    1325                1330                1335

Ala Ser Trp Ala Glu Ile Glu Glu Ala Ala Lys Glu Ala Asn Ile
    1340                1345                1350

His Lys Phe Ile Ser Ala Leu Pro Gln Gly Tyr Glu Thr Gln Val
    1355                1360                1365

Gly Glu Ser Gly Val Gln Leu Ser Gly Gly Gln Lys Gln Arg Ile
    1370                1375                1380

Ala Ile Ala Arg Ala Ile Val Lys Gln Ala Arg Ile Leu Leu Leu
    1385                1390                1395

Asp Glu Ala Ser Ser Ala Leu Asp Leu Glu Ser Glu Arg His Val
    1400                1405                1410

Gln Glu Ala Leu Arg Arg Ala Ser Arg Arg Ala Thr Ala Ile Thr
    1415                1420                1425

Val Ala His Arg Leu Ser Thr Val Arg Asp Ala Asp Arg Ile Ala
    1430                1435                1440

Val Val Ser Ala Gly Arg Val Val Glu Phe Gly Gly His Asp Ala
    1445                1450                1455

Leu Leu Ala Gly His Gly Asp Gly Leu Tyr Ala Ala Met Val Lys
    1460                1465                1470

Ala Glu Thr Glu Ala Gln Ala Phe Lys
    1475                1480

<210> SEQ ID NO 19
<211> LENGTH: 24
<212> TYPE: DNA
<213> ORGANISM: Artificial Sequence
<220> FEATURE:
<223> OTHER INFORMATION: Forward primer for cloning gDNA of OsDN-DTP12
      gene

<400> SEQUENCE: 19
gatagtaatt aagagaccat ggtg                                        24

<210> SEQ ID NO 20
<211> LENGTH: 24
<212> TYPE: DNA
<213> ORGANISM: Artificial Sequence
<220> FEATURE:
<223> OTHER INFORMATION: Reverse primer for cloning gDNA of OsDN-DTP12
      gene
```

```
<400> SEQUENCE: 20
ctgtgcgcac tactcctata tacg                                          24

<210> SEQ ID NO 21
<211> LENGTH: 23
<212> TYPE: DNA
<213> ORGANISM: Artificial Sequence
<220> FEATURE:
<223> OTHER INFORMATION: Forward primer for cloning cDNA of OsSSL13 gene

<400> SEQUENCE: 21
ctctgcgtgc aaattccgtc ttc                                           23

<210> SEQ ID NO 22
<211> LENGTH: 25
<212> TYPE: DNA
<213> ORGANISM: Artificial Sequence
<220> FEATURE:
<223> OTHER INFORMATION: Reverse primer for cloning cDNA of OsSSL13 gene

<400> SEQUENCE: 22
gatcaccagg cactttctat gatgg                                         25

<210> SEQ ID NO 23
<211> LENGTH: 30
<212> TYPE: DNA
<213> ORGANISM: Artificial Sequence
<220> FEATURE:
<223> OTHER INFORMATION: Forward primer for cloning gDNA of truncated
      OsGDSL gene

<400> SEQUENCE: 23
aatgcaaatc agtgacaaca actaactaag                                    30

<210> SEQ ID NO 24
<211> LENGTH: 26
<212> TYPE: DNA
<213> ORGANISM: Artificial Sequence
<220> FEATURE:
<223> OTHER INFORMATION: Reverse primer for cloning gDNA of truncated
      OsGDSL gene

<400> SEQUENCE: 24
gctttgatcg tataatcacc aacatg                                        26

<210> SEQ ID NO 25
<211> LENGTH: 34
<212> TYPE: DNA
<213> ORGANISM: Artificial Sequence
<220> FEATURE:
<223> OTHER INFORMATION: Forward primer for cloning gDNA of OsDN-DTP9
      gene

<400> SEQUENCE: 25
ctgctgaggc ggatagacaa tggcgtataa atcg                               34

<210> SEQ ID NO 26
<211> LENGTH: 33
<212> TYPE: DNA
<213> ORGANISM: Artificial Sequence
<220> FEATURE:
<223> OTHER INFORMATION: Reverse primer for cloning gDNA of OsDN-DTP9
      gene

<400> SEQUENCE: 26
ccgctgaggc accacaaaac cctacccctg aac                                33
```

<210> SEQ ID NO 27
<211> LENGTH: 34
<212> TYPE: DNA
<213> ORGANISM: Artificial Sequence
<220> FEATURE:
<223> OTHER INFORMATION: Forward primer for cloning gDNA of OsWD40-42
     gene

<400> SEQUENCE: 27
ctgctgaggg aatccttctc catctccggt cagc                                34

<210> SEQ ID NO 28
<211> LENGTH: 37
<212> TYPE: DNA
<213> ORGANISM: Artificial Sequence
<220> FEATURE:
<223> OTHER INFORMATION: Reverse primer for cloning gDNA of OsWD40-42
     gene

<400> SEQUENCE: 28
ccgctgaggg cataattctc agtcgctcca gttatcc                             37

<210> SEQ ID NO 29
<211> LENGTH: 33
<212> TYPE: DNA
<213> ORGANISM: Artificial Sequence
<220> FEATURE:
<223> OTHER INFORMATION: Forward primer for cloning gDNA of OsABCB12
     gene

<400> SEQUENCE: 29
ctgctgaggg acatgtcgtg gcagagctca gtg                                 33

<210> SEQ ID NO 30
<211> LENGTH: 34
<212> TYPE: DNA
<213> ORGANISM: Artificial Sequence
<220> FEATURE:
<223> OTHER INFORMATION: Reverse primer for cloning gDNA of OsABCB12
     gene

<400> SEQUENCE: 30
ccgctgaggg tgttataatt gcaaatcccc cagc                                34

<210> SEQ ID NO 31
<211> LENGTH: 18
<212> TYPE: DNA
<213> ORGANISM: Artificial Sequence
<220> FEATURE:
<223> OTHER INFORMATION: Forward primer for real-time RT-PCR analysis of
     OsDN-DTP12 gene

<400> SEQUENCE: 31
cgaggacctt gagcaacc                                                  18

<210> SEQ ID NO 32
<211> LENGTH: 22
<212> TYPE: DNA
<213> ORGANISM: Artificial Sequence
<220> FEATURE:
<223> OTHER INFORMATION: Reverse primer for real-time RT-PCR analysis of
     OsDN-DTP12 gene

<400> SEQUENCE: 32
gccatactct ccccatcaat tc                                             22

<210> SEQ ID NO 33
<211> LENGTH: 19
<212> TYPE: DNA
<213> ORGANISM: Artificial Sequence
<220> FEATURE:
<223> OTHER INFORMATION: Forward primer for real-time RT-PCR analysis of
      OsSSL13 gene

<400> SEQUENCE: 33
ctacttcaag ctgcccctg                                              19

<210> SEQ ID NO 34
<211> LENGTH: 18
<212> TYPE: DNA
<213> ORGANISM: Artificial Sequence
<220> FEATURE:
<223> OTHER INFORMATION: Reverse primer for real-time RT-PCR analysis of
      OsSSL13 gene

<400> SEQUENCE: 34
ctccctcacc tcgctcac                                               18

<210> SEQ ID NO 35
<211> LENGTH: 19
<212> TYPE: DNA
<213> ORGANISM: Artificial Sequence
<220> FEATURE:
<223> OTHER INFORMATION: Forward primer for real-time RT-PCR analysis of
      truncated OsGDSL gene

<400> SEQUENCE: 35
atttcccgcc ttatggtcg                                              19

<210> SEQ ID NO 36
<211> LENGTH: 22
<212> TYPE: DNA
<213> ORGANISM: Artificial Sequence
<220> FEATURE:
<223> OTHER INFORMATION: Reverse primer for real-time RT-PCR analysis of
      truncated OsGDSL gene

<400> SEQUENCE: 36
gatcaatggt gtaggtggag tc                                          22

<210> SEQ ID NO 37
<211> LENGTH: 21
<212> TYPE: DNA
<213> ORGANISM: Artificial Sequence
<220> FEATURE:
<223> OTHER INFORMATION: Forward primer for real-time RT-PCR analysis of
      OsDN-DTP9 gene

<400> SEQUENCE: 37
tgaagggatg aggataggga c                                           21

<210> SEQ ID NO 38
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsDN-DTP9 gene

<400> SEQUENCE: 38
ctcacatttc ccctctccg                                              19

```
<210> SEQ ID NO 39
<211> LENGTH: 22
<212> TYPE: DNA
<213> ORGANISM: Artificial Sequence
<220> FEATURE:
<223> OTHER INFORMATION: Forward primer for real-time RT-PCR analysis of
      OsWD40-42 gene

<400> SEQUENCE: 39
gacatttcaa acattccgtg gg                                              22

<210> SEQ ID NO 40
<211> LENGTH: 21
<212> TYPE: DNA
<213> ORGANISM: Artificial Sequence
<220> FEATURE:
<223> OTHER INFORMATION: Reverse primer for real-time RT-PCR analysis of
      OsWD40-42 gene

<400> SEQUENCE: 40
aatgctggag ttgatggaga c                                               21

<210> SEQ ID NO 41
<211> LENGTH: 18
<212> TYPE: DNA
<213> ORGANISM: Artificial Sequence
<220> FEATURE:
<223> OTHER INFORMATION: Forward primer for real-time RT-PCR analysis of
      OsABCB12 gene

<400> SEQUENCE: 41
gggtgcagtt gtcaggtg                                                   18

<210> SEQ ID NO 42
<211> LENGTH: 19
<212> TYPE: DNA
<213> ORGANISM: Artificial Sequence
<220> FEATURE:
<223> OTHER INFORMATION: Reverse primer for real-time RT-PCR analysis of
      OsABCB12 gene

<400> SEQUENCE: 42
gtatcctcgc ctgcttcac                                                  19
```

ABIOTIC STRESS TOLERANT PLANTS AND POLYNUCLEOTIDES TO IMPROVE ABIOTIC STRESS AND METHODS

FIELD

The field of the disclosure relates to plant breeding and genetics and, particularly, relates to recombinant DNA constructs useful in plants for improving tolerance to abiotic stress, such as drought and cold stress.

BACKGROUND

Stresses to plants may be caused by both biotic and abiotic agents. For example, biotic stresses include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249). Plants are sessile and have to adjust to the prevailing environmental conditions of their surroundings. This has led to their development of a great plasticity in gene regulation, morphogenesis, and metabolism. Adaption and defense strategies involve the activation of genes encoding proteins important in the acclimation or defense towards the different stresses.

Drought is one of the major abiotic stresses that limit crop productivity worldwide, and exposure of plants to a water-limiting environment during various developmental stages appear to activate various physiological and developmental changes. Genetic research has shown that drought tolerance is a quantitative trait, controlled by many genes. Molecular marker-assisted breeding has led to improved drought tolerance in crops, and transgenic approaches to engineer drought tolerance in crops have made progress (Vinocur B. and Altman A. (2005) Curr. Opin. Biotechnol. 16:123-132; Lawlor DW. (2013) J. Exp. Bot. 64:83-108). However, there is a need to develop new compositions and methods to improve drought tolerance in crops. This invention provides such compositions and methods.

SUMMARY

The following embodiments are among those encompassed by the disclosure:

In one embodiment, the present disclosure includes an isolated polynucleotide, comprising: (a) a polynucleotide with a nucleotide sequence of at least 85% identity to SEQ ID NO: 1, 4, 7, 10, 13 or 16; (b) a polynucleotide with a nucleotide sequence of at least 85% identity to SEQ ID NO: 2, 5, 8, 11, 14 or 17; (c) a polynucleotide encoding a polypeptide with an amino acid sequence of at least 90% identity to SEQ ID NO: 3, 6, 9, 12, 15 or 18; or (d) the full complement of the nucleotide sequence of (a), (b) or (c), wherein increased expression of the polynucleotide in a plant enhances drought tolerance. In certain embodiments, the isolated polynucleotide comprises the nucleotide sequence of SEQ ID NO: 1, 2, 4, 5, 7, 8, 10, 11, 13, 14 16 or 17; and the polypeptide comprises the amino acid sequence of SEQ ID NO: 3, 6, 9, 12, 15 or 18.

In another embodiment, the present disclosure includes a recombinant DNA construct comprising the isolated polynucleotide, optionally, operably linked to at least one heterologous regulatory element, wherein the polynucleotide comprises (a) a polynucleotide with a nucleotide sequence of at least 85% identity to SEQ ID NO: 1, 2, 4, 5, 7, 8, 10, 11, 13, 14, 16 or 17; (b) a polynucleotide encoding a polypeptide with an amino acid sequence of at least 90% identity to SEQ ID NO: 3, 6, 9, 12, 15 or 18; or (c) the full complement of the nucleotide sequence of (a) or (b).

In another embodiment, the present disclosure includes a modified plant or seed comprising an increased expression of at least one polynucleotide encoding a polypeptide with an amino acid sequence of at least 90% identity to SEQ ID NO: 3, 6, 9, 12, 15 or 18.

In certain embodiments, the modified plant comprises in its genome a recombinant DNA construct comprising a polynucleotide operably linked to at least one heterologous regulatory element, wherein the polynucleotide comprises (a) a polynucleotide with a nucleotide sequence of at least 85% identity to SEQ ID NO: 1, 2, 4, 5, 7, 8, 10, 11, 13, 14, 16 or 17; (b) a polynucleotide encoding a polypeptide with an amino acid sequence of at least 90% identity to SEQ ID NO: 3, 6, 9, 12, 15 or 18; or (c) the full complement of the nucleotide sequence of (a) or (b).

In certain embodiments, the modified plant comprises targeted genetic modification at a genomic locus that encodes a polynucleotide encoding a polypeptide with an amino acid sequence of at least 90% sequence identity to SEQ ID NO: 3, 6, 9, 12, 15 or 18; wherein the targeted genetic modification increases the level and/or activity of the encoded polypeptide.

In certain embodiments, the modified plant exhibits improved drought tolerance (e.g., increased survival rate, reduced leaf rolling degree, improved seed setting rate, and/or increased grain yield) compared to a control plant. In certain embodiments, the modified plant exhibits improved grain yield when grown under no abiotic stress conditions.

In another embodiment, methods are provided for increasing drought tolerance in a plant, the method comprises increasing the expression of at least one polynucleotide encoding a polypeptide with an amino acid sequence of at least 90% identity to SEQ ID NO: 3, 6, 9, 12, 15 or 18. Wherein the obtained plant exhibits increased drought tolerance when compared to the control plant, and the said improved drought tolerance may be increased survival rate, reduced leaf rolling degree, improved seed setting rate, or increased grain yield under drought conditions.

In certain embodiments, the expression of the polynucleotide is increased by a step selected from the group consisting of: (a) increasing the expression of the polynucleotide by introducing a recombinant DNA construct into the plant, wherein the recombinant DNA construct comprises a polynucleotide encoding a polypeptide having an amino acid sequence of at least 90% identity compared to SEQ ID NOs: 3, 6, 9, 12, 15 or 18 operably linked to at least one heterologous regulatory element; or (b) increasing the expression of an endogenous polynucleotide encoding the polypeptide having an amino acid sequence of at least 90% identity compared to SEQ ID NO: 3, 6, 9, 12, 15 or 18.

In another embodiment, methods are provided for enhancing grain yield in a rice plant, when compared to a control plant, wherein the plant exhibits enhanced grain yield under normal and/or stress conditions, the method comprising increasing the expression of at least one polynucleotide encoding a polypeptide with an amino acid sequence of at least 90% identity to SEQ ID NOs: 3, 6, 9, 12, 15 or 18 in the plant.

In another embodiment, methods are provided for making a plant in which the expression or the activity of a polypeptide having an amino acid sequence of at least 90% identity compared to SEQ ID NOs: 3, 6, 9, 12, 15 or 18 is increased, when compared to the expression or activity of the corresponding polypeptide from a control plant, wherein the plant exhibits at least one phenotype selected from the group consisting of: increased drought tolerance, increased grain yield, increased abiotic stress tolerance and increased biomass, compared to the control plant, wherein the method comprises the steps of (i) introducing a DNA fragment or deleting a DNA fragment or (ii) introducing one or more nucleotide changes in the genomic region comprising the endogenous gene encoding the polypeptide and its regulatory element, wherein the change is effective for increasing the expression or the activity of the endogenous polypeptide. In certain embodiments, wherein the change is introduced using zinc finger nuclease, Transcription Activator-Like Effector Nuclease (TALEN), CRISPR-cas, guided Cas endonuclease, meganuclease or CRISPR-Cas ribonucleoprotein complexes.

In certain embodiments, the plant for use in the compositions and methods is selected from the group consisting of rice, maize, soybean, sunflower, sorghum, canola, wheat, alfalfa, cotton, barley, millet, sugar cane and switchgrass.

In another embodiment, methods are provided for identifying one or more alleles associated with increased grain yield in a population of rice plants, the method comprising: (a) detecting in a population of rice plants one or more polymorphisms in (i) a genomic region encoding a polypeptide or (ii) a regulatory region controlling expression of the polypeptide, wherein the polypeptide comprises the amino acid sequence selected from the group consisting of SEQ ID NO: 3, 6, 9, 12, 15 or 18, or a sequence that is 90% identical to SEQ ID NO: 3, 6, 9, 12, 15 or 18, wherein the one or more polymorphisms in the genomic region encoding the polypeptide or in the regulatory region controlling expression of the polypeptide is associated with grain yield; and (b) identifying one or more alleles at the one or more polymorphisms that are associated with increased grain yield, wherein the one or more alleles associated with increased grain yield is used for marker assisted selection of a rice plant with increased grain yield, the one or more polymorphisms is in the coding region of the polynucleotide, and the regulatory region is a promoter.

BRIEF DESCRIPTION OF THE SEQUENCE LISTING

The disclosure can be more fully understood from the following detailed description and Sequence Listing which form a part of this application.

TABLE 1

SEQ ID NOs for nucleotide and amino acid sequences provided in the sequence listing

| Source species | Sequence Description | SEQ ID NO: (Nucleotide) | SEQ ID NO: (Amino Acid) |
| --- | --- | --- | --- |
| Otyza sativa | OsDN-DTP12 | 1, 2 | 3 |
| Otyza sativa | OsSSL13 | 4, 5 | 6 |
| Otyza sativa | truncated OsGDSL | 7, 8 | 9 |
| Otyza sativa | OsDN-DTP9 | 10, 11 | 12 |
| Otyza sativa | OsWD40-42 | 13, 14 | 15 |
| Otyza sativa | OsABCB12 | 16, 17 | 18 |
| Artificial | Primers | 19-42 | n/a |

The Sequence List contains the one-letter code for nucleotide sequences and the three-letter code for amino acid sequences as defined in conformity with the IUPAC-IUBMB standards described in Nucleic Acids Res. 13:3021-3030 (1985) and in the Biochemical J. 219 (No. 2):345-373 (1984) which are herein incorporated by reference. The symbols and format used for nucleotide and amino acid sequence data comply with the rules set forth in 37 C.F.R.§ 1.822. The official copy of the sequence listing is submitted electronically via EFS-Web as an ASCII formatted sequence listing with a file named RTS22593G-US-PCT Sequence-Listing.txt created on 27 Apr. 2020 and having a size of 52 kilobytes and is filed concurrently with the specification. The sequence listing comprised in this ASCII formatted document is part of the specification and is herein incorporated by reference in its entirety.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsDN-DTP12 (drought tolerance protein 12)" refers to a rice polypeptide that confers drought tolerance phenotype and is encoded by the rice gene locus LOC_Os05g38930.1 and any associated allelic variants thereof. "DN-DTP12 polypeptide" refers herein to the OsDN-DTP12 polypeptide and its homologs from other organisms.

The OsDN-DTP12 polypeptide (SEQ ID NO: 3) is encoded by the coding sequence (CDS) (SEQ ID NO: 2) or nucleotide sequence (SEQ ID NO: 1) at rice gene locus LOC_Os05g38930.1 and any associated allelic variants thereof. This polypeptide is annotated as "hypothetical protein" in TIGR (the internet at plant biology msu.edu/index.shtml).

The term "OsSSL13 (strictosidine synthase like 13)" refers to a rice polypeptide that confers drought tolerance and is encoded by the rice gene locus LOC_OsO3g15710.1 and any associated allelic variants thereof. "SSL13 polypeptide" refers herein to the OsSSL13 polypeptide and its homologs from other organisms.

The OsSSL13 polypeptide (SEQ ID NO: 6) is encoded by the coding sequence (CDS) (SEQ ID NO: 5) or nucleotide sequence (SEQ ID NO: 4) at rice gene locus LOC_OsO3g15710.1 and any associated allelic variants thereof. This polypeptide is annotated as "strictosidine synthase, putative, expressed" in TIGR and "strictosidine synthase like 13" in NCBI (on the world web at ncbi.nlm.nih-.gov), however does not have any prior assigned function.

The term "truncated OsGDSL" refers to a rice polypeptide that confers drought tolerance and is encoded by the first exon of rice gene at locus LOC_Os09g04624.1 and any associated allelic variants thereof.

The truncated OsGDSL polypeptide (SEQ ID NO: 9) is encoded by the coding sequence (CDS) (SEQ ID NO: 8) or nucleotide sequence (SEQ ID NO: 7) at rice gene locus LOC_Os09g04624.1 and any associated allelic variants thereof. The full-length polypeptide is annotated as "GDSL-like lipase/acylhydrolase, putative, expressed" in TIGR.

The term "OsDN-DTP9 (drought tolerance protein 9)" refers to a rice polypeptide that confers drought tolerance phenotype and is encoded by the rice gene locus LOC_Os02g08040.1 and any associated allelic variants thereof. "DN-DTP9 polypeptide" refers herein to the OsDN-DTP9 polypeptide and its homologs from other organisms.

The OsDN-DTP9 polypeptide (SEQ ID NO: 12) is encoded by the coding sequence (CDS) (SEQ ID NO: 11) or nucleotide sequence (SEQ ID NO: 10) at rice gene locus LOC_Os02g08040.1 and any associated allelic variants thereof. This polypeptide is annotated as "expressed protein" in TIGR.

The term "OsWD40-42" refers to a rice polypeptide that confers drought tolerance and is encoded by the rice gene locus LOC_Os02g20430.1 and any associated allelic variants thereof. "WD40-42 polypeptide" refers herein to the OsWD40-42 polypeptide and its homologs from other organisms.

The OsWD40-42 polypeptide (SEQ ID NO: 15) is encoded by the coding sequence (CDS) (SEQ ID NO: 14) or nucleotide sequence (SEQ ID NO: 13) at rice gene locus LOC_Os02g20430.1 and any associated allelic variants thereof. This polypeptide is annotated as "WD domain, G-beta repeat domain containing protein, expressed" in TIGR.

The term "OsABCB12 (ABC transporter B type protein 12)" refers to a rice polypeptide that confers drought tolerance and is encoded by the rice gene locus LOC_Os03g08380.1 and any associated allelic variants thereof. "ABCB12 polypeptide" refers herein to the OsABCB12 polypeptide and its homologs from other organisms.

The OsABCB12 polypeptide (SEQ ID NO: 18) is encoded by the coding sequence (CDS) (SEQ ID NO: 17) or nucleotide sequence (SEQ ID NO: 16) at rice gene locus LOC_Os03g08380.1 and any associated allelic variants thereof. This polypeptide is annotated as "ABC transporter, ATP-binding protein, putative, expressed" in TIGR.

The terms "monocot" and "monocotyledonous plant" are used interchangeably herein. A monocot of the current disclosure includes plants of the Gram ineae family.

The terms "dicot" and "dicotyledonous plant" are used interchangeably herein. A dicot of the current disclosure includes the following families: Brassicaceae, Leguminosae, and Solanaceae.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Heterologous" with respect to sequence means a sequence that originates from a foreign species, or, if from the same species, is substantially modified from its native form in composition and/or genomic position by deliberate human intervention.

"Transgenic" refers to any cell, cell line, callus, tissue, plant part or plant, the genome of which has been altered by the presence of a heterologous nucleic acid, such as a recombinant DNA construct.

A "control" or "control plant" or "control plant cell" provides a reference point for measuring changes in phenotype of a subject plant or plant cell in which genetic alteration, such as transformation, has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

In this disclosure, ZH11-TC and DP0158 may be designated as indicate control plants, ZH11-TC represents rice plants generated from tissue cultured Zhonghua 11 and DP0158 represent plants transformed with empty vector of DP0158.

The term "trait" refers to a physiological, morphological, biochemical, or physical characteristic of a plant or particular plant material or cell.

"Phenotype" means the detectable characteristics of a cell or organism.

"Drought" refers to a decrease in water availability to a plant that, especially when prolonged or when occurring during critical growth periods, can cause damage to the plant or prevent its successful growth (e.g., limiting plant growth or seed yield).

"Drought tolerance" reflects a plant's ability to survive under drought conditions without exhibiting substantial physiological or physical deterioration, and/or its ability to recover when water is restored following a period of drought.

"Drought tolerance activity" of a polypeptide indicates that increased expression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than a control plant when water is restored following a period of drought.

"Environmental conditions" refer to conditions under which the plant is grown, such as the availability of water, availability of nutrients, or the presence of insects or disease.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects the ability to survive and/or grow better when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA.

"Genome" as it applies to plant cells encompasses not only chromosomal DNA found within the nucleus, but also organelle DNA found within subcellular components (e.g., mitochondria, plastid) of the cell.

The terms "full complement" and "full-length complement" are used interchangeably herein, and refer to a complement of a given nucleotide sequence, wherein the complement and the nucleotide sequence consist of the same number of nucleotides and are 100% complementary.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases.

"Polypeptide", "peptide", "amino acid sequence" and "protein" are used interchangeably herein to refer to a polymer of amino acid residues. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogonous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory elements and coding sequences that are derived from different sources, or regulatory elements and coding sequences derived from the same source, but arranged in a manner different than that normally found in nature.

"Regulatory elements" refer to nucleotide sequences located upstream (5' non-coding sequences), within, or downstream (3' non-coding sequences) of a coding sequence, and influencing the transcription, RNA processing or stability, or translation of the associated coding sequence. Regulatory elements may include, but are not limited to, promoters, translation leader sequences, introns, and polyadenylation recognition sequences. The terms "regulatory sequence" and "regulatory element" and "regulatory region" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Introduced" in the context of inserting a nucleic acid fragment (e.g., a recombinant DNA construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on one of a pair of homologous chromosomes in a diploid plant, that plant is hemizygous at that locus.

A "gene" refers to a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "genomic locus" as used herein, generally refers to the location on a chromosome of the plant where a gene, such as a polynucleotide encoding a polypeptide described herein, is found.

A "mutated gene" is a gene that has been altered through human intervention. Such a "mutated gene" has a sequence that differs from the sequence of the corresponding non-mutated gene by at least one nucleotide addition, deletion, or substitution.

As "targeted mutation" is a mutation in a native gene that was made by altering a target sequence within the native gene. A targeted mutation can be introduced using any method known in the art or disclosed herein, such as, for example a method involving a double-strand-break-inducing agent that is capable of inducing a double-strand break in the DNA of the target sequence.

"Genetic modification" refers to a change or alteration in the genomic nucleic acid sequence of a plant introduced by deliberate human activity.

A "nuclear localization signal" is a signal peptide which direct the protein to the nucleus (Raikhel. (1992) Plant Phys. 100:1627-1632).

"CRISPR-associated genes" refers to nucleic acid sequences that encode polypeptide components of clustered regularly interspersed short palindromic repeats (CRISPR)-associated systems (Cas), and the genes are generally coupled, associated or close to or in the vicinity of flanking CRISPR loci. The terms "Cas gene", "CRISPR-associated gene" are used interchangeably herein. Examples include, but are not limited to, Cas3 and Cas9, which encode endo-nucleases from the CRISPR type I and type II systems, respectively.

"Cas endonuclease" refers to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell (U.S. 2015/0082478).

"Guide RNA (gRNA)" refers to a crRNA (CRISPR RNA): tracrRNA fused hybrid RNA molecule encoded by a customizable DNA element that, generally, comprises a copy of a spacer sequence which is complementary to the protospacer sequence of the genomic target site, and a binding domain for an associated-Cas endonuclease of the CRISPR complex.

"Guide polynucleotide" refers to a polynucleotide sequence that can form a complex with a Cas endonuclease and enables the Cas endonuclease to recognize and option-ally cleave a DNA target site. The guide polynucleotide can be comprised of a single molecule or a double molecule. The guide polynucleotide sequence can be a RNA sequence, a DNA sequence, or a combination thereof (a RNA-DNA combination sequence). Optionally, the guide polynucle-otide can comprise at least one nucleotide, phosphodiester bond or linkage modification such as, but not limited to, Locked Nucleic Acid (LNA), 5-methyl dC, 2,6-Diaminopu-rine, 2'-Fluoro A, 2'-Fluoro U, 2'-O-Methyl RNA, phospho-rothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotide that solely comprises ribonucleic acids is also referred to as a "guide RNA".

The term "guide polynucleotide/Cas endonuclease sys-tem" refers to a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence.

"Genomic target site" refers to a protospacer and a protospacer adjacent motif (PAM) located in a host genome selected for targeted mutation and/or double-strand break.

"Protospacer" refers to a short DNA sequence (12 to 40 bp) that can be targeted for mutation, and/or double-strand break, mediated by enzymatic cleavage with a CRISPR system endonuclease guided by complementary base-pair-ing with the spacer sequence in the crRNA or sgRNA.

"Protospacer adjacent motif (PAM)" includes a 3 to 8 bp sequence immediately adjacent to the protospacer sequence in the genomic target site.

The term "variable targeting domain" or "VT domain" is used interchangeably herein and includes a nucleotide sequence that is complementary to one strand (nucleotide sequence) of a double strand DNA target site. The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used inter-changeably herein and includes a nucleotide sequence (such as a second nucleotide sequence domain of a guide poly-nucleotide), that interacts with a Cas endonuclease polypep-tide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can com-prise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times-also referred to as CRISPR-repeats) which are partially palindromic. The repeated sequences (usually specific to a species) are interspaced by variable sequences of constant length (typically 20 to 58 bp by depending on the CRISPR locus (WO2007/025097 published Mar. 1, 2007).

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more (patent application WO-PCT PCT/US12/30061 filed on Mar. 22, 2012). Meganucleases have been classified into four families based on conserved sequence motifs, the families are the LAGLIDADG, GIY-YIG, H—N—H, and His-Cys box families. These motifs participate in the coordination of metal ions and hydrolysis of phosphodiester bonds. HEases are notable for their long recognition sites, and for tolerating some sequence polymorphisms in their DNA substrates.

TAL effector nucleases are a new class of sequence-specific nucleases that can be used to make double-strand breaks at specific target sequences in the genome of a plant or other organism. TAL effector nucleases are created by fusing a native or engineered transcription activator-like (TAL) effector, or functional part thereof, to the catalytic domain of an endonuclease, such as, FokI. The unique, modular TAL effector DNA binding domain allows for the design of proteins with potentially any given DNA recognition specificity (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs consist of an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

The terms "target site", "target sequence", "target DNA", "target locus", "genomic target site", "genomic target sequence", and "genomic target locus" are used interchangeably herein and refer to a polynucleotide sequence in the genome (including choloroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Turning Now to the Embodiments:

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12, 15 or 18; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. In certain embodiments, an increased expression of the encoded polypeptide increases plant drought tolerance, and/or paraquat tolerance activity. In certain embodiments, an increased expression of the encoded polypeptide increases plant grain yield under normal conditions.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12, 15 or 18. The polypeptide is preferably a drought tolerance polypeptide. In certain embodiments, an increased expression of the polypeptide increases plant drought tolerance and/or paraquat tolerance activity. In certain embodiments, an increased expression of the encoded polypeptide increases plant grain yield under normal conditions.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, 5, 8, 11, 14 or 17; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 4, 7, 10, 13 or 16; or (iii) a full complement of the nucleic acid sequence of (i) or (ii). Any of the foregoing isolated polynucleotides may be utilized in any recombinant DNA constructs of the present disclosure. The isolated polynucleotide preferably encodes a drought tolerance polypeptide. In certain embodiments, an increased expression of the polynucleotide improves plant drought tolerance and/or paraquat tolerance activity. In certain embodiments, an increased expression of the polynucleotide increases plant grain yield under normal conditions.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Recombinant DNA Constructs:

In one aspect, the present disclosure includes recombinant DNA constructs.

In one embodiment, a recombinant DNA construct comprises a polynucleotide operably linked to at least one regulatory element (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12, 15 or 18; or (ii) a full complement of the nucleic acid sequence of (i).

In another embodiment, a recombinant DNA construct comprises a polynucleotide operably linked to at least one regulatory element (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 2, 5, 8, 11, 14 or 17; (ii) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 1, 4, 7, 10, 13 or 16; or (iii) a full complement of the nucleic acid sequence of (i) or (ii).

In another embodiment, a recombinant DNA construct comprises a polynucleotide operably linked to at least one regulatory element (e.g., a promoter functional in a plant), wherein said polynucleotide encodes a drought tolerance polypeptide. The polypeptide preferably has drought tolerance and/or paraquat tolerance activity. The polynucleotide may be from, for example, *Oryza sativa*, *Arabidopsis thaliana*, *Zea mays*, *Glycine max*, *Glycine tabacina*, *Glycine soja* or *Glycine tomentella*.

Regulatory Elements:

A recombinant DNA construct of the present disclosure may comprise at least one regulatory element.

A regulatory element may be a promoter, enhancer, 5'UTR, or 3'UTR.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may (or may not) have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) Nature Biotechnol. 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006), the maize ROOTMET2 promoter (WO05063998, published Jul. 14, 2005), the CR1B10 promoter (WO06055487, published May 26, 2006), the CRWAQ81 (WO05035770, published Apr. 21, 2005) and the maize ZRP2.47 promoter (NCBI accession number: U38790; GI No. 1063664).

Recombinant DNA constructs of the present disclosure may also include other regulatory elements, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

An enhancer or enhancer element refers to a cis-acting transcriptional regulatory element, a.k.a. cis-element, which confers an aspect of the overall expression pattern, but is usually insufficient alone to drive transcription, of an operably linked polynucleotide sequence. An isolated enhancer element may be fused to a promoter to produce a chimeric promoter cis-element, which confers an aspect of the overall modulation of gene expression. Enhancers are known in the art and include the SV40 enhancer region, the CaMV 35S enhancer element, and the like. Some enhancers are also known to alter normal regulatory element expression patterns, for example, by causing a regulatory element to be expressed constitutively when without the enhancer, the same regulatory element is expressed only in one specific tissue or a few specific tissues. Duplicating the upstream region of the CaMV35S promoter has been shown to increase expression by approximately tenfold (Kay, R. et al., (1987) *Science* 236: 1299-1302).

Compositions:

In hybrid seed propagated crops, mature transgenic plants or genome edited plants can be self-pollinated to produce a homozygous inbred plant. The inbred plant produces seed containing the newly introduced recombinant DNA construct. These seeds can be grown to produce plants that would exhibit an altered agronomic characteristic (e.g., an increased agronomic characteristic optionally under water limiting conditions), or used in a breeding program to produce hybrid seed, which can be grown to produce plants that would exhibit such an altered agronomic characteristic. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A transgenic plant or genome edited (for example, a rice or maize or soybean plant) comprising in its genome a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to SEQ ID NO: 3, 6, 9, 12, 15 or 18, and wherein said plant exhibits increased drought tolerance and/or paraquat tolerance when compared to a control plant.

2. A transgenic plant (for example, a rice or maize or soybean plant) comprising in its genome a recombinant DNA construct comprising a polynucleotide operably linked to at least one regulatory element, optionally a heterologous regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, to SEQ ID NO: 3, 6, 9, 12, 15 or 18, and wherein said plant exhibits increased drought tolerance and/or paraquat tolerance when compared to a control plant.

3. A genome edited transgenic plant (for example, a rice or maize or soybean plant) comprising a targeted genetic modification at a genomic locus that encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity, to SEQ ID NO: 3, 6, 9, 12, 15 or 18, wherein said plant exhibits increased drought tolerance and/or paraquat tolerance when compared to a control plant.

4. Any progeny of the above plants in embodiment 1-3, any seeds of the above plants in embodiment 1-3, any seeds of progeny of the above plants in embodiment 1-3, and cells from any of the above plants in embodiment 1-3 and progeny thereof.

In any of the foregoing embodiment 1-4 or other embodiments, the drought tolerance polypeptide may be from *Oryza sativa, Oryza australiensis, Oryza barthii, Oryza glaberrima* (African rice), *Oryza latifolia, Oryza longistaminata, Oryza meridionalis, Oryza officinalis, Oryza punctata, Oryza rufipogon* (brownbeard or red rice), *Oryza nivara* (Indian wild rice), *Arabidopsis thaliana, Zea mays, Glycine max, Glycine tabacina, Glycine soja* or *Glycine tomentella*.

In any of the foregoing embodiment 1, 2 or 4 or other embodiments, the recombinant DNA construct may comprise at least a promoter functional in a plant as a regulatory element.

In any of the foregoing embodiment 1-4 or other embodiments, the plant may exhibit the alteration of at least one agronomic characteristic when compared, under water limiting conditions, to a control plant.

In any of the foregoing embodiment 1-4 or other embodiments, the plant may exhibit the alteration of at least one agronomic characteristic when compared, under oxidative stress (paraquat) conditions, to a control plant.

The Examples below describe some representative protocols and techniques for simulating drought conditions and/or evaluating drought tolerance; simulating oxidative conditions.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant.

One of ordinary skill in the art would readily recognize a suitable control or reference plant to be utilized when assessing or measuring an agronomic characteristic or phenotype of a transgenic plant using compositions or methods as described herein. For example, by way of non-limiting illustrations:

1. Progeny of a transformed plant which is hem izygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct. The progeny not comprising the recombinant DNA construct is the control or reference plant.

2. Introgression of a recombinant DNA construct into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A plant comprising a recombinant DNA construct: the plant may be assessed or measured relative to a control plant not comprising the recombinant DNA construct but otherwise having a comparable genetic background to the plant (e.g., sharing at least 90%, 91%, 92%, 93%, 94%, 95%, 96%, 97%, 98%, 99%, or 100% sequence identity of nuclear genetic material compared to the plant comprising the recombinant DNA construct).

Methods:

Methods include but are not limited to methods for increasing drought tolerance in a plant, methods for evaluating drought tolerance in a plant, methods for increasing paraquat tolerance, methods for altering an agronomic characteristic in a plant, methods for determining an alteration of an agronomic characteristic in a plant, and methods for producing seed.

Methods include but are not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory element, and wherein the transformed host cell is grown under conditions that are suitable for expression of the recombinant DNA construct.

A method for altering the level of expression of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

One embodiment provides, a method of increasing drought tolerance in a plant, comprising increasing the expression of at least one polynucleotide encoding a polypeptide with an amino acid sequence of at least 90% identity to SEQ ID NO: 3, 6, 9, 12, 15 or 18.

One embodiment provides a method of increasing drought tolerance and/or paraquat tolerance in a plant, comprising: (a) introducing into a regenerable plant cell a recombinant DNA construct comprising a polynucleotide operably linked to at least one regulatory element (for example, a promoter functional in a plant), wherein the polynucleotide encodes a polypeptide having an amino acid sequence of at least 90%, 91%, 92%, 93%, 94%, 95%, 96%, 97%, 98%, 99%, or 100% identity to SEQ ID NO: 3, 6, 9, 12, 15 or 18; (b) generating a transgenic plant from the regenerable plant cell after step (a), wherein the transgenic plant comprises in its genome the recombinant DNA construct and exhibits increased drought tolerance and/or paraquat tolerance when compared to a control plant; and further (c) obtaining a progeny plant derived from transgenic plant, wherein said progeny plant comprises in its genome the recombinant DNA construct and exhibits increased drought tolerance and/or paraquat tolerance when compared to a control plant.

One embodiment provides a method of increasing drought tolerance and/or paraquat tolerance in a plant, comprising: (a) introducing into a regenerable plant cell a targeted genetic modification at a genomic locus that encodes a polypeptide comprising an amino acid sequence having at least 90%, 91%, 92%, 93%, 94%, 95%, 96%, 97%, 98%, 99%, or 100% identity to SEQ ID NO: 3, 6, 9, 12, 15 or 18; and (b) generating the plant, wherein the level and/or activity of the encoded polypeptide is increased in the plant.

A method of evaluating drought tolerance and/or paraquat tolerance in a plant comprising (a) obtaining a transgenic or genome edited plant, which comprises in its genome a polynucleotide operably linked to at least one regulatory element, optionally a heterologous regulatory element (for example, a promoter functional in a plant), wherein said polynucleotide encodes a polypeptide having an amino acid sequence of at least 90%, 91%, 92%, 93%, 94%, 95%, 96%, 97%, 98%, 99%, or 100% identity, to SEQ ID NO: 3, 6, 9, 12, 15 or 18; (b) obtaining a progeny plant derived from said transgenic or genome edited plant, wherein the progeny plant comprises in its genome the recombinant DNA construct; and (c) evaluating the progeny plant for drought tolerance and/or paraquat tolerance compared to a control plant.

A method of determining an alteration of an agronomic characteristic in a plant comprising (a) obtaining a transgenic or genome edited plant which comprises in its genome a polynucleotide operably linked to at least one regulatory element, optionally a heterologous regulatory element (for example, a promoter functional in a plant), wherein said polynucleotide encodes a polypeptide having an amino acid sequence of at least 90%, 91%, 92%, 93%, 94%, 95%, 96%, 97%, 98%, 99%, or 100% identity when compared to SEQ ID NO: 3, 6, 9, 12, 15 or 18; (b) obtaining a progeny plant derived from said transgenic or genome edited plant; and (c) determining whether the progeny plant exhibits an alteration in at least one agronomic characteristic when compared, optionally under water limiting conditions to a control plant.

A method of producing seed comprising any of the preceding methods, and further comprising obtaining seeds from said progeny plant, wherein said seeds comprise in their genome said recombinant DNA construct.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" engineered endonucleases such as meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41). A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326 (5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The CRISPR/Cas system allows targeted cleavage of genomic DNA guided by a customizable small noncoding RNA.

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

Stacking of Traits

Modified plants may comprise a stack of one or more drought tolerance polynucleotides disclosed herein with one or more additional polynucleotides resulting in the production or suppression of multiple polypeptide sequences.

Modified plants comprising stacks of polynucleotide sequences can be obtained by either or both of traditional breeding methods or through genetic engineering methods. These methods include, but are not limited to, breeding individual lines each comprising a polynucleotide of interest, genome editing, transforming a transgenic plant comprising a gene disclosed herein with a subsequent gene and cotransformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences.

EXAMPLES

Example 1

Cloning and Vector Construction of Drought Tolerance Genes

Primers were designed for cloning rice drought tolerance genes OsDN-DTP12, OsSSL13, truncated OsGDSL, OsDN-DTP9, OsWD40-42, and OsABCB12. The primers and the expected-lengths of the amplified genes are shown in Table 2.

OsSSL13 cDNAs was cloned using pooled cDNA from leaf, stem and root tissues of Zhonghua 11 plant as the template. OsDN-DTP12, truncated OsGDSL, OsDN-DTP9, OsWD40-42, and OsABCB12 gDNAs were cloned, and amplified using genomic DNA of Zhonghua 11 as the template.

TABLE 2

Primers for cloning rice drought tolerance genes

| Primer | Sequence | SEQ ID NO: | Gene name | Length of amplified fragment (bp) |
|---|---|---|---|---|
| gc-6598 | 5'-GATAGTAATTAAGAGACCATGGTG-3' | 19 | OsDN-DTP12 | 387 |
| gc-6599 | 5'-CTGTGCGCACTACTCCTATATACG-3' | 20 | | |
| gc-6388 | 5'-CTCTGCGTGCAAATTCCGTCTTC-3' | 21 | OsSSL13 | 1417 |
| gc-6389 | 5'-GATCACCAGGCACTTTCTATGATGG-3' | 22 | | |
| gc-6428 | 5'-AATGCAAATCAGTGACAACAACTAACTAAG-3' | 23 | Truncated OsGDSL | 534 |
| gc-6429 | 5'-GCTTTGATCGTATAATCACCAACATG-3' | 24 | | |
| gc-7713 | 5'-CTGCTGAGGCGGATAGACAATGGCGTATAAATCG-3' | 25 | OsDN-DTP9 | 238 |
| gc-7714 | 5'-CCGCTGAGGCACCACAAAACCCTACCCCTGAAC-3' | 26 | | |
| gc-7723 | 5'-CTGCTGAGGGAATCCTTCTCCATCTCCGGTCAGC-3' | 27 | OsWD40-42 | 2685 |
| gc-7724 | 5'-CCGCTGAGGGCATAATTCTCAGTCGCTCCAGTTATCC-3' | 28 | | |
| gc-6403 | 5'-CTGCTGAGGGACATGTCGTGGCAGAGCTCAGTG-3' | 29 | OsABCB12 | 5476 |
| gc-6404 | 5'-CCGCTGAGGGTGTTATAATTGCAAATCCCCCAGC-3' | 30 | | |

The PCR amplified products were extracted after the agarose gel electrophoresis using a column kit and then ligated with TA cloning vectors. The sequences and orientation in these constructs were confirmed by sequencing. Then these genes were cloned into plant binary construct DP0158 (pCAMBIA1300-DsRed).

The cloned nucleotide sequence in construct of DP0797 and coding sequence of OsDN-DTP12 are provided as SEQ ID NO: 1 and 2, the encoded amino acid sequence of OsDN-DTP12 is shown in SEQ ID NO: 3; the cloned nucleotide sequence in construct of DP0800 and coding sequence of OsSSL13 are provided as SEQ ID NO: 4 and 5, the encoded amino acid sequence of OsSSL13 is shown in SEQ ID NO: 6; the cloned nucleotide sequence in construct of DP0802 and coding sequence of truncated OsGDSL are provided as SEQ ID NO: 7 and 8, the encoded amino acid sequence of truncated OsGDSL is shown in SEQ ID NO: 9; the cloned nucleotide sequence in construct of DP0949 and coding sequence of OsDN-DTP9 are provided as SEQ ID NO: 10 and 11, the encoded amino acid sequence of OsDN-DTP9 is shown in SEQ ID NO: 12; the cloned nucleotide sequence in construct of DP0950 and coding sequence of OsWD40-42 are provided as SEQ ID NO: 13 and 14, the encoded amino acid sequence of OsWD40-42 is shown in SEQ ID NO: 15; and the cloned nucleotide sequence in construct of DP1169 and coding sequence of OsABCB12 are provided as SEQ ID NO: 16 and 17, the encoded amino acid sequence of OsABCB12 is shown in SEQ ID NO: 18.

Example 2

Generation of Rice Plants with Increased Gene Expression

The over-expression vectors and empty vector (DP0158) were transformed into the Zhonghua 11 (*Oryza sativa* L.) by Agrobacteria-mediated method as described by Lin and Zhang ((2005) *Plant Cell Rep.* 23:540-547). Zhonghua 11 was cultivated by the Institute of Crop Sciences, Chinese Academy of Agricultural Sciences. The first batch of seeds used in this research was provided by Beijing Weiming Kaituo Agriculture Biotech Co., Ltd. Calli induced from embryos was transformed with Agrobacteria with the vector. The transgenic seedlings (T0) generated in transformation laboratory are transplanted in the field to get T1 seeds. The T1 and T2 seeds are stored at cold room (4° C.). The over-expression vectors contain marker genes. T1 and T2 seeds which showed red color under green fluorescent light were transgenic seeds and were used in the following trait screening.

Example 3

Gene Expression Analysis

The gene expression levels in the transgenic rice plants were analyzed. A standard RT-PCR or a real-time RT-PCR procedure was used. EF-1α gene was used as an internal control to show that the amplification and loading of samples from the transgenic rice and the controls were similar. Gene expression was normalized based on the EF-1α mRNA levels.

The relative expression levels of OsDN-DTP12 gene in leaves of different transgenic rice lines were determined by real-time PCR analyses. The base level of expression in ZH11-TC was set at 1.00, and the expression levels in other OsDN-DTP12 lines increased from about 6-fold to 2256-fold compared to ZH11-TC. ZH11-TC is tissue cultured ZH11 rice and DP0158 is empty vector transformed ZH11 rice plants. The primers for real-time RT-PCR for the OsDN-DTP12 gene in the over-expression transgenic rice are listed below:

```
                                       (SEQ ID NO: 31)
    DP0797-F1: 5'-CGAGGACCTTGAGCAACC-3'

(SEQ ID NO: 32)
    DP0797-R1: 5'-GCCATACTCTCCCCATCAATTC-3'
```

The relative expression levels of OsSSL13 gene in leaves of different transgenic rice lines were determined by real-time PCR analyses and increased from about 23-fold to 426-fold as compared to the base expression level in ZH11-TC (control; set at 1.00). OsSSL13 over-expressed in almost all the tested transgenic rice lines. The primers used for the real-time PCR are as below:

```
                                       (SEQ ID NO: 33)
    DP0800-F2: 5'-CTACTTCAAGCTGCCCCTG-3'

(SEQ ID NO: 34)
    DP0800-R2: 5'-CTCCCTCACCTCGCTCAC-3'
```

The relative expression levels of truncated OsGDSL gene in leaves of different transgenic rice lines were determined by real-time PCR analyses and increased from about 9-fold to 9477-fold as compared to the base expression level in ZH11-TC (control; set at 1.00). Truncated OsGDSL over-expressed in all the transgenic lines.

```
                                       (SEQ ID NO: 35)
    DP0802-F1: 5'-ATTTCCCGCCTTATGGTCG-3'

(SEQ ID NO: 36)
    DP0802-R1: 5'-GATCAATGGTGTAGGTGGAGTC-3'
```

The relative expression levels of OsDN-DTP9 gene in leaves of different transgenic rice lines were determined by real-time PCR analyses and increased from about 83-fold to 13144-fold as compared to the base expression level in ZH11-TC (control; set at 1.00). The expression levels of OsDN-DTP9 are higher than that in ZH11-TC seedlings.

```
                                       (SEQ ID NO: 37)
    DP0949-F1: 5'-TGAAGGGATGAGGATAGGGAC-3'

(SEQ ID NO: 38)
    DP0949-R1: 5'-CTCACATTTCCCCTCTCCG-3'
```

The relative expression levels of OsWD40-42 gene in leaves of different transgenic rice lines were determined by real-time PCR analyses and increased from about 197-fold to 927-fold as compared to the base expression level in ZH11-TC (control; set at 1.00).

```
                                       (SEQ ID NO: 39)
    DP0950-F1: 5'-GACATTTCAAACATTCCGTGGG-3'

(SEQ ID NO: 40)
    DP0950-R1: 5'-AATGCTGGAGTTGATGGAGAC-3'
```

The relative expression levels of OsABCB12 gene in leaves of different transgenic rice lines were determined by real-time PCR analyses and increased from about 39-fold to 2365-fold as compared to the base expression level in DP0158 (control; set at 1.00). OsABCB12 over-expressed in most the transgenic rice lines, while the expression of OsABCB12 was low in DP0158 plants.

```
                                       (SEQ ID NO: 41)
    DP1169-F1: 5'-GGGTGCAGTTGTCAGGTG-3'

(SEQ ID NO: 42)
    DP1169-R1: 5'-GTATCCTCGCCTGCTTCAC-3'
```

Example 4

Field Drought Assays of Mature Transgenic Rice Plants

Flowering stage drought stress is an important problem in agriculture practice. The transgenic rice plants were tested under field drought conditions. For the Field drought assays of mature rice plants, 12 transgenic lines from each gene construct were tested. The T2 seeds were first sterilized, and the germinated seeds were planted in a seedbed field. At 3-leaf stage, the seedlings were transplanted into the testing field with 4 replicates and 10 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Watering was stopped at the panicle initiation stage, so as to give drought stress at flowering stage depending on the weather conditions (temperature and humidity). The soil water content was measured every 4 days at about 10 sites per block using TDR30 (Spectrum Technologies, Inc.).

Plant phenotypes were observed and recorded during the experiments. The phenotypes include heading date, leaf rolling degree, drought sensitivity and drought tolerance. Special attention was paid to leaf rolling degree at noontime. At the end of the growing season, six representative plants of each transgenic line were harvested from the middle of the row per line, and grain yield per plant was measured. The grain yield data were statistically analyzed using mixed linear model. Positive transgenic lines were selected based on the analysis (P<0.1).

Field Drought (DRT) Assay Results:

1) Field DRT validation results of OsDN-DTP12 (DP0797) transgenic rice Twelve OsDN-DTP12 transgenic rice plants were tested in Hainan field. ZH11-TC and DP0158 rice plants planted nearby were used as controls. When the main stem panicles reached panicle initiation stage II-IV, and the tiller panicles reached panicle initiation stage I, watering was stopped. The soil volumetric water content decreased from 40% to 10% during panicle heading stage. 19 days after stopping watering, the main stem panicles reached panicle initiation stage VIII, and the tiller panicles reached panicle initiation stage V-VI, and the rice plants began to show leaf roll phenotype. 35 days after stopping watering, 50% panicles headed out. Five OsDN-DTP12 transgenic lines DP0797.02, DP0797.03, DP0797.04, DP0797.06 and DP0797.14 showed better seed setting at the maturation stage.

The grain yield analysis showed that the grain yield per plant of OsDN-DTP12 transgenic rice was greater than ZH11-TC control and significantly greater than DP0158 control at the construct level. Three OsDN-DTP12 transgenic lines showed significantly greater grain yields per plant than ZH11-TC plants, and six OsDN-DTP12 transgenic lines showed significantly greater grain yields per plant than DP0158 control plants (Table 3). These results indicate that OsDN-DTP12 transgenic rice plant is tolerance to drought conditions, and over-expression of OsDN-DTP12 increased drought tolerance and increased the grain yield per plant after drought stress at flowering stage.

TABLE 3

Grain yield analysis of OsDN-DTP12 transgenic rice plants under field drought conditions (1$^{st}$ experiment)

| Line ID | Number of survival plants | Number of harvested plants | Yield per plant (g) | CK = ZH11-TC | | | CK = DP0158 | | |
| --- | --- | --- | --- | --- | --- | --- | --- | --- | --- |
| | | | | Diff | P value | P ≤ 0.1 | Diff | P value | P ≤ 0.1 |
| DP0797 (Construct) | 462 | 287 | 6.90 | 0.62 | 0.484 | | 1.72 | 0.053 | Y |
| ZH11-TC | 40 | 24 | 6.28 | | | | | | |
| DP0158 | 40 | 24 | 5.18 | | | | | | |
| DP0797.01 | 36 | 24 | 5.52 | −0.75 | 0.437 | | 0.34 | 0.723 | |
| DP0797.02 | 38 | 24 | 7.67 | 1.39 | 0.152 | | 2.49 | 0.010 | Y |
| DP0797.03 | 40 | 24 | 8.82 | 2.55 | 0.009 | Y | 3.65 | 0.000 | Y |
| DP0797.04 | 40 | 24 | 9.22 | 2.94 | 0.002 | Y | 4.04 | 0.000 | Y |
| DP0797.06 | 40 | 24 | 8.29 | 2.02 | 0.038 | Y | 3.12 | 0.001 | Y |
| DP0797.07 | 40 | 23 | 6.48 | 0.21 | 0.828 | | 1.30 | 0.179 | |
| DP0797.10 | 40 | 24 | 5.52 | −0.75 | 0.430 | | 0.35 | 0.716 | |
| DP0797.11 | 38 | 24 | 5.80 | −0.48 | 0.624 | | 0.62 | 0.524 | |
| DP0797.12 | 40 | 24 | 4.58 | −1.69 | 0.076 | | −0.60 | 0.539 | |
| DP0797.13 | 33 | 24 | 6.97 | 0.70 | 0.465 | | 1.79 | 0.060 | Y |
| DP0797.14 | 37 | 24 | 7.18 | 0.90 | 0.353 | | 2.00 | 0.036 | Y |
| DP0797.15 | 40 | 24 | 6.71 | 0.43 | 0.655 | | 1.53 | 0.113 | |

The same 12 OsDN-DTP12 transgenic rice plants were tested again in Hainan field. Watering was stopped when the main stem panicles reached panicle initiation stage III-IV and the tiller panicles reached panicle initiation stage I-II. 52 days after stopping watering, the main stem panicles reached milk mature stage, and the rice plants started to show drought stress phenotype. The soil volumetric water content decreased from 18% to 6% during heading and maturation stage. Four OsDN-DTP12 transgenic lines DP0797.02, DP0797.03, DP0797.04, and DP0797.06 showed better seed setting at the maturation stage.

Grain yield analysis showed that OsDN-DTP12 transgenic rice plants exhibited greater grain yield per plant than ZH11-TC and DP0158 controls at the construct level. Four OsDN-DTP12 transgenic lines exhibited significantly greater grain yields per plant than ZH11-TC and DP0158 controls at the line level (Table 4). These results indicate that OsDN-DTP12 transgenic rice plant gained drought tolerance and exhibited greater grain yield increase per plant.

TABLE 4

Grain yield analysis of OsDN-DTP12 transgenic rice plants under field drought conditions (2$^{nd}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0797 (Construct) | 476 | 287 | 5.52 | 0.10 | 0.912 | | 1.31 | 0.139 | |
| ZH11-TC | 39 | 24 | 5.42 | | | | | | |
| DP0158 | 38 | 24 | 4.21 | | | | | | |
| DP0797.01 | 40 | 24 | 3.85 | −1.58 | 0.105 | | −0.37 | 0.708 | |
| DP0797.02 | 40 | 24 | 7.31 | 1.88 | 0.054 | Y | 3.09 | 0.002 | Y |
| DP0797.03 | 40 | 24 | 8.31 | 2.88 | 0.003 | Y | 4.09 | 0.000 | Y |
| DP0797.04 | 40 | 24 | 7.24 | 1.82 | 0.064 | Y | 3.03 | 0.002 | Y |
| DP0797.06 | 40 | 24 | 7.41 | 1.99 | 0.042 | Y | 3.20 | 0.001 | Y |
| DP0797.07 | 40 | 24 | 3.41 | −2.01 | 0.040 | | −0.80 | 0.413 | |
| DP0797.10 | 40 | 24 | 3.69 | −1.73 | 0.077 | | −0.52 | 0.597 | |
| DP0797.11 | 39 | 24 | 5.18 | −0.24 | 0.807 | | 0.97 | 0.321 | |
| DP0797.12 | 40 | 24 | 3.54 | −1.88 | 0.055 | | −0.67 | 0.495 | |
| DP0797.13 | 37 | 23 | 4.73 | −0.70 | 0.475 | | 0.51 | 0.599 | |
| DP0797.14 | 40 | 24 | 6.97 | 1.55 | 0.114 | | 2.76 | 0.005 | Y |
| DP0797.15 | 40 | 24 | 4.61 | −0.81 | 0.412 | | 0.40 | 0.682 | |

2) Field DRT Validation Results of OsSSL13 (DP0800) Transgenic Rice

Twelve OsSSL13 transgenic rice plants were tested in Hainan field. ZH11-TC and DP0158 rice plants planted nearby were used as controls. When the main stem panicles reached panicle initiation stage II-IV, and the tiller panicles reached panicle initiation stage I, watering was stopped. The soil volumetric water content decreased from 40% to 10% during panicle heading stage. 19 days after stopping watering, the main stem panicles reached panicle initiation stage VIII, and the tiller panicles reached panicle initiation stage V-VI, and the rice plants began to show leaf roll phenotype. 35 days after stopping watering, 50% panicles headed out. Two OsSSL13 transgenic lines DP0800.07 and DP0800.10 showed better seed setting at the maturation stage.

The grain yield analysis showed that the grain yield per plant of OsSSL13 transgenic rice was significantly greater than both ZH11-TC and DP0158 control at the construct level. Seven OsSSL13 transgenic lines showed significantly greater grain yields per plant than ZH11-TC plants, and nine OsSSL13 transgenic lines showed significantly greater grain yields per plant than DP0158 control plants (Table 5). These results indicate that OsSSL13 transgenic rice plant is tolerance to drought conditions, and over-expression of OsSSL13 increased drought tolerance at seedling stage and increased the grain yield per plant after drought stress at flowering stage.

TABLE 5

Grain yield analysis of OsSSL13 transgenic rice plants under field drought conditions (1$^{st}$ experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0800 (Construct) | 468 | 288 | 6.98 | 1.62 | 0.069 | Y | 2.96 | 0.001 | Y |
| ZH11-TC | 39 | 25 | 5.36 | | | | | | |
| DP0158 | 40 | 24 | 4.02 | | | | | | |
| DP0800.01 | 36 | 23 | 7.15 | 1.80 | 0.07 | Y | 3.13 | 0.001 | Y |
| DP0800.02 | 38 | 24 | 4.99 | −0.37 | 0.70 | | 0.97 | 0.310 | |
| DP0800.03 | 39 | 24 | 6.63 | 1.27 | 0.19 | | 2.61 | 0.007 | Y |
| DP0800.05 | 38 | 24 | 6.89 | 1.54 | 0.11 | | 2.87 | 0.003 | Y |
| DP0800.06 | 40 | 25 | 7.56 | 2.20 | 0.02 | Y | 3.54 | 0.000 | Y |
| DP0800.07 | 39 | 24 | 7.71 | 2.35 | 0.02 | Y | 3.69 | 0.000 | Y |
| DP0800.08 | 40 | 24 | 7.32 | 1.97 | 0.04 | Y | 3.30 | 0.001 | Y |
| DP0800.10 | 40 | 24 | 8.63 | 3.27 | 0.00 | Y | 4.61 | 0.000 | Y |
| DP0800.11 | 40 | 24 | 5.41 | 0.06 | 0.95 | | 1.39 | 0.142 | |
| DP0800.12 | 40 | 24 | 4.99 | −0.37 | 0.70 | | 0.97 | 0.316 | |
| DP0800.14 | 40 | 24 | 7.77 | 2.41 | 0.012 | Y | 3.75 | 0.000 | Y |
| DP0800.15 | 38 | 24 | 8.71 | 3.36 | 0.001 | Y | 4.69 | 0.000 | Y |

The same 12 OsSSL13 transgenic rice plants were tested again in Hainan field. Watering was stopped when the main stem panicles reached panicle initiation stage V-VI and the tiller panicles reached panicle initiation stage II-III. 49 days after stopping watering, the main stem panicles reached milk mature stage, and the rice plants started to show drought stress phenotype. The soil volumetric water content decreased from 21% to 7% during heading and maturation stage. One OsSSL13 transgenic line DP0800.10 exhibited good seed setting phenotype.

Grain yield analysis showed that OsSSL13 transgenic rice plants exhibited greater grain yield per plant than ZH11-TC control and significantly greater grain yield per plant than DP0158 control at the construct level. Three OsSSL13 transgenic lines exhibited significantly greater grain yields per plant than ZH11-TC and six lines exhibited significantly greater grain yields per plant than DP0158 controls at the line level (Table 6). These results further indicate that OsSSL13 transgenic rice plant gained drought tolerance and exhibited greater grain yield increase per plant.

main stem panicles headed out, the tiller panicles were at panicle initiation stage VI-VIE, and some rice plants exhibited phenotypes such as leaf rolling. At the end of the planting season, the transgenic rice plants DP0802.03, DP0802.07, DP0802.11, DP0802.14 and DP0802.15 exhibited good seed setting rate.

The grain yield per plant is shown in Table 7, the truncated OsGDSL transgenic rice plants showed greater grain yield per plant than ZH11-TC and significantly greater grain yield per plant than DP0158 plants at the construct

TABLE 6

Grain yield analysis of OsSSL13 transgenic rice plants under field drought conditions ($2^{nd}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0800 (Construct) | 480 | 288 | 6.46 | 0.33 | 0.743 | | 1.76 | 0.077 | Y |
| ZH11-TC | 40 | 24 | 6.14 | | | | | | |
| DP0158 | 40 | 24 | 4.70 | | | | | | |
| DP0800.01 | 40 | 24 | 6.86 | 0.72 | 0.499 | | 2.16 | 0.043 | Y |
| DP0800.02 | 40 | 24 | 3.13 | −3.01 | 0.005 | | −1.57 | 0.142 | |
| DP0800.03 | 40 | 24 | 5.48 | −0.66 | 0.537 | | 0.78 | 0.456 | |
| DP0800.04 | 40 | 24 | 5.78 | −0.36 | 0.736 | | 1.08 | 0.310 | |
| DP0800.06 | 40 | 24 | 8.44 | 2.31 | 0.028 | Y | 3.74 | 0.000 | Y |
| DP0800.08 | 40 | 24 | 6.15 | 0.01 | 0.992 | | 1.45 | 0.168 | |
| DP0800.09 | 40 | 24 | 4.84 | −1.30 | 0.216 | | 0.13 | 0.899 | |
| DP0800.10 | 40 | 24 | 9.13 | 2.99 | 0.005 | Y | 4.43 | 0.000 | Y |
| DP0800.11 | 40 | 24 | 6.70 | 0.56 | 0.594 | | 2.00 | 0.060 | Y |
| DP0800.12 | 40 | 24 | 4.94 | −1.20 | 0.260 | | 0.24 | 0.824 | |
| DP0800.14 | 40 | 24 | 7.39 | 1.26 | 0.237 | | 2.69 | 0.010 | Y |
| DP0800.15 | 40 | 24 | 8.74 | 2.60 | 0.014 | Y | 4.03 | 0.000 | Y |

3) Field DRT Validation Results of Truncated OsGDSL (DP0802) Transgenic Rice

Twelve truncated OsGDSL transgenic lines were tested in Hainan Province in the first experiment. Watering was stopped from initiation stage II of the main stem panicle to seed maturity to produce heavier drought stress. The soil volumetric water content decreased from 36% to 10% during heading stage. 26 days after stopping watering, the level. Six truncated OsGDSL transgenic rice lines showed significantly greater grain yield per plant than ZH11-TC plants, and nine transgenic lines showed significantly greater grain yield per plant than DP0158 plants at the line level. These results indicate that truncated OsGDSL transgenic rice plant had greater grain yield per plant than controls after drought stress.

TABLE 7

Grain yield analysis of truncated OsGDSL transgenic rice plants under field drought conditions ($1^{st}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0802 (Construct) | 465 | 282 | 6.51 | 1.09 | 0.152 | | 1.62 | 0.036 | Y |
| ZH11-TC | 40 | 24 | 5.42 | | | | | | |
| DP0158 | 40 | 24 | 4.89 | | | | | | |
| DP0802.02 | 40 | 24 | 6.91 | 1.49 | 0.069 | Y | 2.02 | 0.011 | Y |
| DP0802.03 | 40 | 24 | 7.61 | 2.20 | 0.007 | Y | 2.73 | 0.001 | Y |
| DP0802.05 | 40 | 24 | 5.32 | −0.10 | 0.904 | | 0.43 | 0.600 | |
| DP0802.06 | 40 | 24 | 4.57 | −0.84 | 0.294 | | −0.32 | 0.701 | |
| DP0802.07 | 26 | 17 | 7.81 | 2.39 | 0.005 | Y | 2.92 | 0.001 | Y |
| DP0802.08 | 40 | 24 | 5.41 | 0.00 | 0.997 | | 0.52 | 0.524 | |
| DP0802.09 | 40 | 25 | 6.34 | 0.92 | 0.262 | | 1.45 | 0.079 | Y |
| DP0802.11 | 40 | 24 | 7.54 | 2.12 | 0.008 | Y | 2.65 | 0.001 | Y |
| DP0802.12 | 40 | 24 | 6.89 | 1.47 | 0.073 | Y | 2.00 | 0.015 | Y |
| DP0802.13 | 39 | 24 | 7.00 | 1.58 | 0.049 | Y | 2.11 | 0.011 | Y |
| DP0802.14 | 40 | 24 | 6.36 | 0.95 | 0.239 | | 1.47 | 0.073 | Y |
| DP0802.15 | 40 | 24 | 6.33 | 0.92 | 0.261 | | 1.45 | 0.079 | Y |

The second experiment was performed in Hainan province; twelve truncated OsGDSL transgenic lines were tested. When the main stem panicles reached panicle initiation stage V-VI and the tiller panicles reached panicle initiation stage II-DI, watering was stopped. The soil volumetric water content decreased from 21% to 7% during panicle heading and maturation stage. 27 days after stopping watering, 50% rice panicles headed out, and 52 days after stopping water, the main stem panicles reached milk mature stage, and the rice plants showed leaf rolling phenotype.

As shown in Table 8, truncated OsGDSL transgenic rice exhibited significantly greater grain yield per plant than ZH11-TC and DP0158 controls at the construct level. Seven lines had significantly greater grain yields per plant than DP0158 control, and six lines had significantly greater grain yield per plant than ZH11-TC control. These results further demonstrate that truncated OsGDSL rice plant is tolerance to drought stress, and over-expression of truncated OsGDSL increases the grain yield per plant after drought stress at flowering and heading stage.

soil volumetric water content decreased from 45% to 10% before panicle heading and the rainfall resulted in variation of the soil volumetric water content between 25% and 10% during drought stress. 16 days after stopping watering, the main stem panicles reached panicle initiation stage IV-V, the tiller panicles reached panicle initiation stage DI-IV, and the rice plants began to show leaf roll phenotype. Six transgenic lines DP0949.01, DP0949.02, DP0949.06, DP0949.14, DP0949.15 and DP0949.17 showed less leaf roll degree and greener than control. At the maturation stage, DP0949.17 showed better seed setting phenotype.

At the end of the growing season, about six representative plants from each transgenic line were harvested from the middle of the row per line, and grain yield per plant was measured. The grain yield per plant of OsDN-DTP9 transgenic rice was greater than DP0158 control at the construct level. One OsDN-DTP9 transgenic lines showed significantly greater grain yield per plant than ZH11-TC plants, and five transgenic lines showed significantly greater grain yield per plant than DP0158 control plants (Table 9). These

TABLE 8

Grain yield analysis of truncated OsGDSL transgenic rice plants under field drought conditions ($2^{nd}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0802 (Construct) | 470 | 285 | 6.14 | 1.88 | 0.058 | Y | 2.33 | 0.019 | Y |
| ZH11-TC | 40 | 24 | 4.26 | | | | | | |
| DP0158 | 40 | 24 | 3.81 | | | | | | |
| DP0802.02 | 40 | 24 | 4.72 | 0.47 | 0.662 | | 0.91 | 0.385 | |
| DP0802.03 | 40 | 24 | 7.43 | 3.17 | 0.003 | Y | 3.62 | 0.001 | Y |
| DP0802.06 | 40 | 24 | 5.42 | 1.16 | 0.276 | | 1.61 | 0.131 | |
| DP0802.07 | 40 | 24 | 8.07 | 3.81 | 0.000 | Y | 4.26 | 0.000 | Y |
| DP0802.08 | 40 | 24 | 4.99 | 0.74 | 0.483 | | 1.18 | 0.266 | |
| DP0802.09 | 31 | 19 | 6.88 | 2.62 | 0.013 | Y | 3.07 | 0.004 | Y |
| DP0802.10 | 40 | 24 | 2.29 | −1.97 | 0.060 | | −1.52 | 0.153 | |
| DP0802.11 | 40 | 24 | 9.36 | 5.10 | 0.000 | Y | 5.55 | 0.000 | Y |
| DP0802.12 | 40 | 24 | 5.64 | 1.39 | 0.184 | | 1.83 | 0.079 | Y |
| DP0802.13 | 40 | 25 | 7.76 | 3.50 | 0.001 | Y | 3.95 | 0.000 | Y |
| DP0802.14 | 39 | 25 | 6.22 | 1.96 | 0.064 | Y | 2.41 | 0.023 | Y |
| DP0802.15 | 40 | 24 | 4.92 | 0.67 | 0.523 | | 1.11 | 0.287 | |

4) Field DRT Validation Results of OsDN-DTP9 (DP0949) Transgenic Rice

Twelve OsDN-DTP9 transgenic rice plants were tested in Ningxia field, ZH11-TC and DP0158 rice plants planted nearby were used as controls. When the main stem panicles reached panicle initiation stage I, watering was stopped. The results indicate that OsDN-DTP9 transgenic rice plant is tolerance to drought conditions, and over-expression of OsDN-DTP9 increased drought tolerance at seedling stage and may increase the grain yield per plant after drought stress at flowering stage.

TABLE 9

Grain yield analysis of OsDN-DTP9 transgenic rice plants under field drought conditions ($1^{st}$ experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0949 (Construct) | 462 | 278 | 1.35 | −0.33 | 0.682 | | 1.09 | 0.177 | |
| ZH11-TC | 38 | 21 | 1.68 | | | | | | |
| DP0158 | 27 | 17 | 0.26 | | | | | | |
| DP0949.01 | 39 | 23 | 1.88 | 0.20 | 0.807 | | 1.62 | 0.055 | Y |
| DP0949.02 | 39 | 24 | 1.72 | 0.04 | 0.959 | | 1.46 | 0.082 | Y |
| DP0949.06 | 38 | 24 | 1.24 | −0.43 | 0.605 | | 0.98 | 0.241 | |
| DP0949.07 | 40 | 24 | 0.45 | −1.22 | 0.144 | | 0.19 | 0.820 | |

TABLE 9-continued

Grain yield analysis of OsDN-DTP9 transgenic rice
plants under field drought conditions (1st experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0949.08 | 38 | 22 | 1.15 | −0.52 | 0.533 | | 0.89 | 0.287 | |
| DP0949.11 | 38 | 23 | 0.78 | −0.89 | 0.286 | | 0.52 | 0.537 | |
| DP0949.12 | 37 | 22 | 0.55 | −1.13 | 0.179 | | 0.29 | 0.731 | |
| DP0949.13 | 35 | 23 | 0.57 | −1.11 | 0.185 | | 0.30 | 0.716 | |
| DP0949.14 | 37 | 21 | 1.80 | 0.13 | 0.881 | | 1.54 | 0.066 | Y |
| DP0949.15 | 41 | 24 | 1.88 | 0.20 | 0.810 | | 1.62 | 0.055 | Y |
| DP0949.16 | 39 | 24 | 1.04 | −0.64 | 0.448 | | 0.78 | 0.352 | |
| DP0949.17 | 41 | 24 | 3.09 | 1.42 | 0.097 | Y | 2.83 | 0.001 | Y |

The second experiment was performed in Hainan province, the same twelve OsDN-DTP9 transgenic lines were tested. When the main stem panicles reached panicle initiation stage III-IV, and the tiller panicles reached panicle initiation stage I-II, watering was stopped. The soil volumetric water content decreased from 24% to 8% during panicle heading and maturation stage. 27 days after stopping watering, 50% rice panicles headed out. 49 days after stopping watering, the main stem panicles reached milk mature stage, and the rice plants showed leaf rolling phenotype. Many transgenic lines showed good seed setting phenotypes.

As shown in Table 10, OsDN-DTP9 transgenic rice exhibited greater grain yield per plant than ZH11-TC control and significantly greater grain yield per plant than DP0158 control at the construct level. Three OsDN-DTP9 transgenic lines had significantly greater grain yields per plant than ZH11-TC control, and nine lines had significantly greater grain yields per plant than DP0158 control. These results further demonstrate that OsDN-DTP9 transgenic rice plant is tolerance to drought conditions, and over-expression of OsDN-DTP9 increases the grain yield per plant after drought stress at flowering and heading stage.

5) Field DRT Validation Results of OsWD40-42 (DP0950) Transgenic Rice

Twelve OsWD40-42 transgenic lines were tested in Ningxia in the first experiment. Watering was stopped when the main stem panicles reached panicle initiation I. The soil volumetric water content decreased from 45% to 10% before panicle heading and the rainfall resulted in variation of the soil volumetric water content between 25% and 10% during drought stress. 16 days after stopping watering, the main stem panicles reached panicle initiation stage IV-V, the tiller panicles reached panicle initiation stage DI-IV, and the rice plants began to show leaf roll phenotype. Almost all the OsWD40-42 transgenic rice lines showed good seed setting phenotypes at the maturation stage.

As shown in Table 11, the OsWD40-42 transgenic rice plants showed greater grain yield per plant than ZH11-TC control and significantly greater grain yield per plant than DP0158 control at the construct level. Six transgenic lines exhibited significantly greater grain yields per plant than both ZH11-TC and DP0158 controls at the line level. These results demonstrate that OsWD40-42 transgenic rice plant is tolerant to drought stress and over-expression of OsWD40-42 increased the grain yield per plant after drought stress at flowering stage.

TABLE 10

Grain yield analysis of OsDN-DTP9 transgenic rice
plants under field drought conditions (2nd experiment)

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP0949 (Construct) | 480 | 288 | 5.82 | 0.19 | 0.818 | | 2.44 | 0.003 | Y |
| ZH11-TC | 40 | 24 | 5.64 | | | | | | |
| DP0158 | 40 | 24 | 3.38 | | | | | | |
| DP0949.01 | 40 | 24 | 5.50 | −0.13 | 0.886 | | 2.12 | 0.020 | Y |
| DP0949.02 | 40 | 24 | 7.48 | 1.84 | 0.047 | Y | 4.10 | 0.000 | Y |
| DP0949.06 | 40 | 24 | 6.01 | 0.38 | 0.684 | | 2.63 | 0.004 | Y |
| DP0949.07 | 40 | 24 | 3.84 | −1.80 | 0.052 | | 0.46 | 0.619 | |
| DP0949.08 | 40 | 24 | 6.15 | 0.51 | 0.581 | | 2.77 | 0.003 | Y |
| DP0949.11 | 40 | 24 | 4.84 | −0.80 | 0.382 | | 1.46 | 0.111 | |
| DP0949.12 | 40 | 24 | 5.13 | −0.51 | 0.583 | | 1.75 | 0.057 | Y |
| DP0949.13 | 40 | 24 | 5.61 | −0.03 | 0.974 | | 2.23 | 0.015 | Y |
| DP0949.14 | 40 | 24 | 7.29 | 1.66 | 0.070 | Y | 3.91 | 0.000 | Y |
| DP0949.15 | 40 | 24 | 5.52 | −0.12 | 0.900 | | 2.14 | 0.019 | Y |
| DP0949.16 | 40 | 24 | 4.13 | −1.50 | 0.099 | | 0.75 | 0.404 | |
| DP0949.17 | 40 | 24 | 8.39 | 2.75 | 0.002 | Y | 5.01 | 0.000 | Y |

TABLE 11

Grain yield analysis of OsWD40-42 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0950 (Construct) | 474 | 271 | 3.69 | 1.07 | 0.183 | | 3.01 | 0.000 | Y |
| ZH11-TC | 39 | 20 | 2.62 | | | | | | |
| DP0158 | 40 | 23 | 0.68 | | | | | | |
| DP0950.01 | 37 | 23 | 4.20 | 1.58 | 0.061 | Y | 3.52 | 0.000 | Y |
| DP0950.03 | 40 | 24 | 2.88 | 0.26 | 0.758 | | 2.19 | 0.009 | Y |
| DP0950.04 | 39 | 23 | 3.53 | 0.91 | 0.275 | | 2.85 | 0.001 | Y |
| DP0950.05 | 37 | 21 | 4.76 | 2.14 | 0.010 | Y | 4.08 | 0.000 | Y |
| DP0950.06 | 42 | 24 | 2.36 | −0.26 | 0.755 | | 1.67 | 0.046 | Y |
| DP0950.09 | 40 | 21 | 5.88 | 3.26 | 0.000 | Y | 5.20 | 0.000 | Y |
| DP0950.10 | 40 | 24 | 6.90 | 4.28 | 0.000 | Y | 6.22 | 0.000 | Y |
| DP0950.11 | 40 | 21 | 2.31 | −0.30 | 0.718 | | 1.63 | 0.051 | Y |
| DP0950.12 | 41 | 23 | 4.02 | 1.40 | 0.095 | Y | 3.34 | 0.000 | Y |
| DP0950.14 | 40 | 23 | 2.08 | −0.54 | 0.522 | | 1.40 | 0.097 | Y |
| DP0950.15 | 39 | 21 | 4.05 | 1.43 | 0.090 | Y | 3.37 | 0.000 | Y |
| DP0950.16 | 39 | 23 | 1.30 | −1.32 | 0.115 | | 0.62 | 0.462 | |

The second experiment was performed in Hainan province; the same twelve OsWD40-42 transgenic lines were tested. Watering was stopped when the main stem panicles reached to panicle initiation stage III-IV and the tiller panicles reached to panicle initiation stage I-II. The soil volumetric water content decreased from 24% to 8% during panicle heading and maturation stage. 27 days after stopping watering, 50% rice panicles headed out. 49 days after stopping watering, the main stem panicles reached milk mature stage, and the rice plants showed leaf rolling phenotype. Four OsWD40-42 transgenic lines DP0950.01, DP0950.03, DP0950.05 and DP0950.10 showed good seed setting phenotypes.

The OsWD40-42 transgenic rice plants showed greater grain yield per plant than ZH11-TC control and significantly greater grain yield per plant than DP0158 control at the construct level. Analysis at line level showed that three OsWD40-42 transgenic lines showed significantly greater grain yield per plant than the ZH11-TC control, and five transgenic lines showed significantly greater grain yield per plant than DP0158 control plants (Table 12). These results further demonstrate that OsWD40-42 over-expressed transgenic rice plant is tolerant to drought stress, and over-expression of OsWD40-42 increased the drought tolerance and then increased the grain yield per plant.

TABLE 12

Grain yield analysis of OsWD40-42 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP0950 (Construct) | 460 | 282 | 5.06 | 1.26 | 0.122 | | 1.67 | 0.041 | Y |
| ZH11-TC | 40 | 24 | 3.80 | | | | | | |
| DP0158 | 40 | 24 | 3.40 | | | | | | |
| DP0950.01 | 40 | 24 | 7.28 | 3.48 | 0.000 | Y | 3.88 | 0.000 | Y |
| DP0950.03 | 39 | 24 | 5.08 | 1.28 | 0.167 | | 1.68 | 0.068 | Y |
| DP0950.04 | 39 | 24 | 4.48 | 0.68 | 0.461 | | 1.08 | 0.234 | |
| DP0950.05 | 40 | 24 | 7.73 | 3.93 | 0.000 | Y | 4.33 | 0.000 | Y |
| DP0950.06 | 38 | 24 | 4.19 | 0.39 | 0.674 | | 0.79 | 0.390 | |
| DP0950.09 | 38 | 24 | 4.60 | 0.80 | 0.385 | | 1.20 | 0.190 | |
| DP0950.10 | 40 | 24 | 7.51 | 3.71 | 0.000 | Y | 4.11 | 0.000 | Y |
| DP0950.11 | 40 | 24 | 4.95 | 1.15 | 0.203 | | 1.56 | 0.090 | Y |
| DP0950.12 | 38 | 24 | 4.86 | 1.06 | 0.249 | | 1.46 | 0.108 | |
| DP0950.14 | 30 | 18 | 3.96 | 0.16 | 0.870 | | 0.56 | 0.559 | |
| DP0950.15 | 40 | 24 | 3.38 | −0.42 | 0.642 | | −0.02 | 0.983 | |
| DP0950.16 | 38 | 24 | 2.75 | −1.05 | 0.253 | | −0.64 | 0.479 | |

6) Field DRT Validation Results of OsABCB12 (DP1169) Transgenic Rice

Twelve OsABCB12 transgenic rice plants were tested in Hainan field. ZH11-TC and DP0158 rice plants planted nearby were used as controls. When the main stem panicles reached panicle initiation stage II-III, watering was stopped. The soil volumetric water content decreased from 35% to 8% during panicle heading and maturation stage. 26 days after stopping watering, the main stem panicles headed out, the tiller panicles reached panicle initiation stage VI-VII, and the rice plants began to show leaf roll phenotype. 39 days after stopping watering, 50% rice panicles headed out. Three OsABCB12 transgenic lines DP1169.02, DP1169.09 and DP1169.12 showed better seed setting at the maturation stage.

The grain yield analysis showed that the grain yield per plant of OsABCB12 transgenic rice was significantly greater than both ZH11-TC and DP0158 control at the construct level. Ten OsABCB12 transgenic lines showed significantly greater grain yields per plants than ZH11-TC plants, and eleven OsABCB12 transgenic lines showed significantly greater grain yields per plants than DP0158 control plants (Table 13). These results indicate that OsABCB12 transgenic rice plant is tolerance to drought conditions, and over-expression of OsABCB12 increased drought tolerance at seedling stage and increased the grain yield per plant after drought stress at flowering stage.

TABLE 13

Grain yield analysis of OsABCB12 transgenic rice plants under field drought conditions (1st experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1169 (Construct) | 463 | 288 | 6.57 | 2.52 | 0.001 | Y | 2.65 | 0.001 | Y |
| ZH11-TC | 40 | 24 | 4.04 | | | | | | |
| DP0158 | 38 | 24 | 3.92 | | | | | | |
| DP1169.02 | 40 | 24 | 9.16 | 5.12 | 0.000 | Y | 5.25 | 0.000 | Y |
| DP1169.03 | 40 | 24 | 6.71 | 2.67 | 0.001 | Y | 2.80 | 0.001 | Y |
| DP1169.04 | 38 | 24 | 6.93 | 2.89 | 0.000 | Y | 3.01 | 0.000 | Y |
| DP1169.06 | 38 | 24 | 5.70 | 1.66 | 0.036 | Y | 1.79 | 0.027 | Y |
| DP1169.07 | 40 | 24 | 5.81 | 1.76 | 0.033 | Y | 1.89 | 0.022 | Y |
| DP1169.09 | 38 | 24 | 7.78 | 3.74 | 0.000 | Y | 3.86 | 0.000 | Y |
| DP1169.10 | 36 | 24 | 6.72 | 2.67 | 0.001 | Y | 2.80 | 0.001 | Y |
| DP1169.11 | 40 | 24 | 7.19 | 3.15 | 0.000 | Y | 3.27 | 0.000 | Y |
| DP1169.12 | 40 | 24 | 8.40 | 4.35 | 0.000 | Y | 4.48 | 0.000 | Y |
| DP1169.13 | 39 | 24 | 5.33 | 1.28 | 0.120 | | 1.41 | 0.081 | Y |
| DP1169.14 | 36 | 24 | 3.37 | −0.67 | 0.405 | | −0.54 | 0.498 | |
| DP1169.15 | 38 | 24 | 5.67 | 1.63 | 0.046 | Y | 1.76 | 0.029 | Y |

The same 12 OsABCB12 transgenic rice plants were tested again in Hainan field. Watering was stopped when the main stem panicles reached panicle initiation stage V-VI and the tiller panicles reached panicle initiation stage II-III. 27 days after stopping watering, 50% rice panicles headed out. 49 days after stopping watering, the main stem panicles reached milk mature stage, and the rice plants started to show drought stress phenotype. The soil volumetric water content decreased from 21% to 7% during heading stage.

Grain yield analysis showed that OsABCB12 transgenic rice plants exhibited significantly greater grain yield per plant than ZH11-TC and DP0158 controls at the construct level. Seven OsABCB12 transgenic lines exhibited significantly greater grain yields per plant than ZH11-TC and ten OsABCB12 transgenic lines exhibited significantly greater grain yields per plant than DP0158 controls at the line level (Table 14). These results further indicate that OsABCB12 transgenic rice plant gained drought tolerance and exhibited greater grain yield increase per plant.

TABLE 14

Grain yield analysis of OsABCB12 transgenic rice plants under field drought conditions (2nd experiment)

| Line ID | Number of survival plants | Number of harvested plants | Yield per plant (g) | CK = ZH11-TC Diff | P value | P ≤ 0.1 | CK = DP0158 Diff | P value | P ≤ 0.1 |
|---|---|---|---|---|---|---|---|---|---|
| DP1169 (Construct) | 474 | 289 | 6.31 | 1.95 | 0.050 | Y | 3.53 | 0.000 | Y |
| ZH11-TC | 39 | 24 | 4.36 | | | | | | |
| DP0158 | 40 | 24 | 2.78 | | | | | | |
| DP1169.02 | 39 | 24 | 9.61 | 5.25 | 0.000 | Y | 6.83 | 0.000 | Y |
| DP1169.03 | 40 | 24 | 6.85 | 2.50 | 0.018 | Y | 4.08 | 0.000 | Y |
| DP1169.04 | 40 | 24 | 7.56 | 3.20 | 0.003 | Y | 4.78 | 0.000 | Y |
| DP1169.06 | 40 | 24 | 4.82 | 0.46 | 0.664 | | 2.04 | 0.053 | Y |
| DP1169.07 | 39 | 24 | 5.28 | 0.93 | 0.385 | | 2.51 | 0.018 | Y |
| DP1169.09 | 37 | 24 | 6.05 | 1.70 | 0.112 | | 3.28 | 0.002 | Y |
| DP1169.10 | 40 | 24 | 6.81 | 2.45 | 0.020 | Y | 4.03 | 0.000 | Y |
| DP1169.11 | 40 | 24 | 3.92 | −0.43 | 0.683 | | 1.15 | 0.280 | |
| DP1169.12 | 40 | 25 | 8.02 | 3.67 | 0.001 | Y | 5.25 | 0.000 | Y |
| DP1169.13 | 40 | 24 | 6.39 | 2.04 | 0.054 | Y | 3.62 | 0.001 | Y |
| DP1169.14 | 39 | 24 | 3.82 | −0.54 | 0.607 | | 1.04 | 0.320 | |
| DP1169.15 | 40 | 24 | 6.60 | 2.25 | 0.032 | Y | 3.82 | 0.000 | Y |

Example 5

Laboratory Paraquat Assays of Transgenic Rice Plants

Paraquat (1,1-dimethyl-4,4-bipyridinium dichloride), is a foliar-applied and non-selective bipyridinium herbicide, and it is one of the most widely used herbicides in the world, controlling weeds in a huge variety of crops like corn, rice, soybean etc. In plant cells, paraquat mainly targets chloroplasts by accepting electrons from photosystem I and then reacting with oxygen to produce superoxide and hydrogen peroxide, which cause photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds book). Therefore, the paraquat tolerance of the drought tolerant transgenic rice plants was tested.

Paraquat Assay Methods:

Transgenic rice plants from ten transgenic lines were tested by paraquat assay. Tissue-cultured Zhonghua 11 plants (ZH11-TC) and empty vector transgenic plants (DP0158) were used as controls. T2 seeds were sterilized and germinated, and this assay was carried out in growth room with temperature at 28~30° C. and humidity ~30%. The germinated seeds were placed in a tube with a hole at the bottom, and water cultured at 30° C. for 5 days till one-leaf and one-terminal bud stage. Uniform seedlings about 3.5~4 cm in height were selected for paraquat testing. Randomized block design was used in this experiment. There were five blocks, each of which has 16×12 holes. Each transgenic line was placed in one row (12 plants/line), and ZH11-TC and DP0158 seedlings were placed in 3 rows (3×12 plants) randomly in one block. Then the seedlings were treated with 0.8 µM paraquat solution for 7 days at 10 h day/14 h night, and the treated seedlings first encountered dark and took up the paraquat solution which was changed every two days. After treated for 7 days, the green seedlings were counted. Those seedlings that maintain green in whole without damage were considered as paraquat tolerant seedling; those with bleached leaves or stem were not considered as paraquat tolerant seedling.

Tolerance rate was used as a parameter for this trait screen, which is the percentage of plants which kept green and showed tolerant phenotype over the total plant number.

The data was analyzed at construct level (all transgenic plants compared with the control) and transgenic line level (different transgenic lines compared with the control) using a statistic model of "Y~seg+line (seg)+rep+error", random effect of "rep", Statistic Method of "SAS® PROC GLIMMIX".

Paraquat Assay Results:

1) Paraquat Validation Results of OsDN-DTP12 (DP0797) Transgenic Rice

In the first experiment, after paraquat solution treated for seven days, 345 of the 600 OsDN-DTP12 transgenic seedlings (58%) kept green and showed tolerant phenotype, while 91 of the 180 (51%) seedlings from ZH11-TC showed tolerant phenotype, and 92 of the 180 (51%) DP0158 seedlings showed tolerant phenotype. The tolerance rate of all screened OsDN-DTP12 transgenic seedlings was greater than ZH11-TC and DP0158 controls at the construct level.

Further analysis at transgenic line level indicates that seven OsDN-DTP12 transgenic lines had greater tolerance rates than ZH11-TC and DP0158 controls and two lines had significantly greater tolerance rates than ZH11-TC and DP0158 controls (Table 15). These results demonstrate that OsDN-DTP12 transgenic rice plants had enhanced paraquat tolerance compared to both controls of ZH11-TC and DP0158 rice plants at construct and transgenic line level at seedling stages. OsDN-DTP12 may function in enhancing paraquat tolerance or antioxidative ability of transgenic plants.

TABLE 15

Paraquat tolerance assay of OsDN-DTP12 transgenic rice plants
($1^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0797 (Construct) | 345 | 600 | 58 | 0.0938 | | 0.1211 | |
| ZH11-TC | 91 | 180 | 51 | | | | |
| DP0158 | 92 | 180 | 51 | | | | |
| DP0797.01 | 27 | 60 | 45 | 0.4594 | | 0.4161 | |
| DP0797.02 | 38 | 60 | 63 | 0.0921 | | 0.1064 | |
| DP0797.03 | 33 | 60 | 55 | 0.5530 | | 0.6033 | |
| DP0797.04 | 31 | 60 | 52 | 0.8817 | | 0.9405 | |
| DP0797.06 | 35 | 60 | 58 | 0.3009 | | 0.3361 | |
| DP0797.07 | 42 | 60 | 70 | 0.0119 | Y | 0.0143 | Y |
| DP0797.10 | 43 | 60 | 72 | 0.0067 | Y | 0.0081 | Y |
| DP0797.11 | 30 | 60 | 50 | 0.9411 | | 0.8822 | |
| DP0797.12 | 37 | 60 | 62 | 0.1416 | | 0.1618 | |
| DP0797.13 | 29 | 60 | 48 | 0.7669 | | 0.7110 | |

In the second experiment, ten same OsDN-DTP12 transgenic lines were tested. Seven days later, 427 of the 600 OsDN-DTP12 transgenic seedlings (71%) kept green and showed tolerant phenotype, while 108 of the 180 (60%) seedlings from ZH11-TC showed tolerant phenotype, and 96 of the 180 (53%) DP0158 seedlings showed tolerant phenotype. The tolerance rate of all screened OsDN-DTP12 transgenic seedlings was significantly greater than ZH11-TC and DP0158 controls at the construct level.

Further analysis at transgenic line level indicates that three OsDN-DTP12 transgenic lines had significantly greater tolerance rates than ZH11-TC control and six lines had significantly greater tolerance rates than DP0158 control (Table 16). These results further demonstrate that OsDN-DTP12 functions in enhancing paraquat tolerance or antioxidative ability of transgenic plants.

TABLE 16

Paraquat tolerance assay of OsDN-DTP12 transgenic rice plants ($2^{nd}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0797 (Construct) | 427 | 600 | 71 | 0.0048 | Y | 0.0000 | Y |
| ZH11-TC | 108 | 180 | 60 | | | | |
| DP0158 | 96 | 180 | 53 | | | | |
| DP0797.01 | 41 | 60 | 68 | 0.2548 | | 0.0479 | Y |
| DP0797.02 | 49 | 60 | 82 | 0.0042 | Y | 0.0004 | Y |
| DP0797.03 | 40 | 60 | 67 | 0.3619 | | 0.0776 | |
| DP0797.04 | 44 | 60 | 73 | 0.0702 | | 0.0094 | Y |
| DP0797.06 | 39 | 60 | 65 | 0.4940 | | 0.1213 | |
| DP0797.07 | 40 | 60 | 67 | 0.3619 | | 0.0776 | |
| DP0797.10 | 45 | 60 | 75 | 0.0424 | Y | 0.0052 | Y |
| DP0797.11 | 48 | 60 | 80 | 0.0078 | Y | 0.0008 | Y |
| DP0797.12 | 37 | 60 | 62 | 0.8199 | | 0.2660 | |
| DP0797.13 | 44 | 60 | 73 | 0.0702 | | 0.0094 | Y |

2) Paraquat Validation Results of OsSSL13 (DP0800) Transgenic Rice

In the first experiment, after paraquat solution treated for seven days, 499 of the 600 OsSSL13 transgenic seedlings (83%) kept green and showed tolerant phenotype, while 108 of the 180 (60%) seedlings from ZH11-TC showed tolerant phenotype, and 114 of the 180 (63%) DP0158 seedlings showed tolerant phenotype. The tolerance rate of all screened OsSSL13 transgenic seedlings was significantly greater than ZH11-TC and DP0158 controls at the construct level.

Further analysis at transgenic line level indicates that nine OsSSL13 transgenic lines had significantly greater tolerance rates than ZH11-TC and DP0158 controls (Table 17). These results demonstrate that OsSSL13 transgenic rice plants had enhanced paraquat tolerance compared to both controls of ZH11-TC and DP0158 rice plants at construct and transgenic line level at seedling stages. OsSSL13 functions in enhancing paraquat tolerance or antioxidative ability of transgenic plants.

TABLE 17

Paraquat tolerance assay of OsSSL13 transgenic rice plants ($1^{st}$ experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0800 (Construct) | 499 | 600 | 83 | 0.0000 | Y | 0.0000 | Y |
| ZH11-TC | 108 | 180 | 60 | | | | |
| DP0158 | 114 | 180 | 63 | | | | |
| DP0800.01 | 49 | 60 | 82 | 0.0044 | Y | 0.0122 | Y |
| DP0800.02 | 50 | 60 | 83 | 0.0024 | Y | 0.0066 | Y |
| DP0800.03 | 50 | 60 | 83 | 0.0024 | Y | 0.0066 | Y |
| DP0800.05 | 50 | 60 | 83 | 0.0024 | Y | 0.0066 | Y |
| DP0800.06 | 47 | 60 | 78 | 0.0293 | Y | 0.0771 | |
| DP0800.07 | 50 | 60 | 83 | 0.0024 | Y | 0.0066 | Y |
| DP0800.08 | 47 | 60 | 78 | 0.0146 | Y | 0.0381 | Y |
| DP0800.10 | 51 | 60 | 85 | 0.0013 | Y | 0.0036 | Y |
| DP0800.11 | 52 | 60 | 87 | 0.0007 | Y | 0.0019 | Y |
| DP0800.12 | 53 | 60 | 88 | 0.0004 | Y | 0.0010 | Y |

In the second experiment, ten same OsSSL13 transgenic lines were tested. Seven days later, 468 of the 600 OsSSL13 transgenic seedlings (78%) kept green and showed tolerant phenotype, while 112 of the 180 (62%) seedlings from ZH11-TC showed tolerant phenotype, and 100 of the 180 (56%) DP0158 seedlings showed tolerant phenotype. The tolerance rate of all screened OsSSL13 transgenic seedlings was significantly greater than ZH11-TC and DP0158 controls at the construct level.

Further analysis at transgenic line level indicates that six OsSSL13 transgenic lines had significantly greater tolerance rates than ZH11-TC control and nine lines had significantly greater tolerance rates than DP0158 control (Table 18). These results further demonstrate that OsSSL13 functions in enhancing paraquat tolerance or antioxidative ability of transgenic plants.

TABLE 18

Paraquat tolerance assay of OsSSL13 transgenic rice plants ($2^{nd}$ experiment)

| Line ID | Number of tolerant seedlings | Number of total seedlings | Tolerance rate (%) | CK = ZH11-TC P value | $P \leq 0.05$ | CK = DP0158 P value | $P \leq 0.05$ |
|---|---|---|---|---|---|---|---|
| DP0800 (Construct) | 468 | 600 | 78 | 0.0000 | Y | 0.0000 | Y |
| ZH11-TC | 112 | 180 | 62 | | | | |
| DP0158 | 100 | 180 | 56 | | | | |
| DP0800.01 | 45 | 60 | 75 | 0.0786 | | 0.0109 | Y |
| DP0800.02 | 45 | 60 | 75 | 0.0786 | | 0.0109 | Y |
| DP0800.03 | 47 | 60 | 78 | 0.0277 | Y | 0.0033 | Y |
| DP0800.05 | 48 | 60 | 80 | 0.0157 | Y | 0.0017 | Y |
| DP0800.06 | 45 | 60 | 75 | 0.0786 | | 0.0109 | Y |
| DP0800.07 | 46 | 60 | 77 | 0.0475 | Y | 0.0060 | Y |
| DP0800.08 | 41 | 60 | 68 | 0.3977 | | 0.0883 | |
| DP0800.10 | 49 | 60 | 82 | 0.0087 | Y | 0.0009 | Y |
| DP0800.11 | 50 | 60 | 83 | 0.0047 | Y | 0.0005 | Y |
| DP0800.12 | 52 | 60 | 87 | 0.0014 | Y | 0.0001 | Y |

3) Paraquat Validation Results of Truncated OsGDSL (DP0802) Transgenic Rice

In the first experiment, after paraquat solution treated for seven days, 476 of the 600 truncated OsGDSL transgenic seedlings (79%) kept green and showed tolerant phenotype, while 120 of the 180 (67%) seedlings from ZH11-TC showed tolerant phenotype, and 108 of the 180 (60%) DP0158 seedlings showed tolerant phenotype. The tolerance rate of all screened truncated OsGDSL transgenic seedlings was significantly greater than ZH11-TC and DP0158 controls at the construct level.

Further analysis at transgenic line level indicates that six truncated OsGDSL transgenic lines had significantly greater tolerance rates than ZH11-TC control and seven lines had significantly greater tolerance rates than DP0158 control (Table 19). These results demonstrate that truncated OsGDSL transgenic rice plants had enhanced paraquat tolerance compared to both controls of ZH11-TC and DP0158 rice plants at construct and transgenic line level at seedling stages. Truncated OsGDSL functions in enhancing paraquat tolerance or antioxidative ability of transgenic plants.

TABLE 19

Paraquat tolerance assay of truncated OsGDSL transgenic rice plants ($1^{st}$ experiment)

| Line ID | Number of tolerant seedlings | Number of total seedlings | Tolerance rate (%) | CK = ZH11-TC P value | $P \leq 0.05$ | CK = DP0158 P value | $P \leq 0.05$ |
|---|---|---|---|---|---|---|---|
| DP0802 | 476 | 600 | 79 | 0.0004 | Y | 0.0000 | Y |
| ZH11-TC | 120 | 180 | 67 | | | | |
| DP0158 | 108 | 180 | 60 | | | | |
| DP0802.02 | 51 | 60 | 85 | 0.0104 | Y | 0.0012 | Y |
| DP0802.03 | 43 | 60 | 72 | 0.4756 | | 0.1121 | |
| DP0802.05 | 54 | 60 | 90 | 0.0017 | Y | 0.0002 | Y |
| DP0802.06 | 50 | 60 | 83 | 0.0190 | Y | 0.0023 | Y |
| DP0802.07 | 49 | 60 | 82 | 0.0338 | Y | 0.0042 | Y |
| DP0802.08 | 50 | 60 | 83 | 0.0190 | Y | 0.0023 | Y |
| DP0802.09 | 41 | 60 | 68 | 0.8127 | | 0.2548 | |

TABLE 19-continued

Paraquat tolerance assay of truncated OsGDSL transgenic rice plants (1st experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0802.11 | 45 | 60 | 75 | 0.2340 | | 0.0424 | Y |
| DP0802.12 | 51 | 60 | 85 | 0.0104 | Y | 0.0012 | Y |
| DP0802.13 | 42 | 60 | 70 | 0.6349 | | 0.1724 | |

In the second experiment, ten same truncated OsGDSL transgenic lines were tested. Seven days later, 496 of the 600 truncated OsGDSL transgenic seedlings (83%) kept green and showed tolerant phenotype, while 122 of the 180 (68%) seedlings from ZH11-TC showed tolerant phenotype, and 130 of the 180 (72%) DP0158 seedlings showed tolerant phenotype. The tolerance rate of all screened truncated OsGDSL transgenic seedlings was significantly greater than ZH11-TC and DP0158 controls at the construct level.

Further analysis at transgenic line level indicates that seven truncated OsGDSL transgenic lines had significantly greater tolerance rates than ZH11-TC control and two lines had significantly greater tolerance rates than DP0158 control (Table 20). These results further demonstrate that truncated OsGDSL functions in enhancing paraquat tolerance or antioxidative ability of transgenic plants.

TABLE 20

Paraquat tolerance assay of truncated OsGDSL transgenic rice plants (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0802 (Construct) | 496 | 600 | 83 | 0.0000 | Y | 0.0040 | Y |
| ZH11-TC | 122 | 180 | 68 | | | | |
| DP0158 | 130 | 180 | 72 | | | | |
| DP0802.02 | 50 | 60 | 83 | 0.0266 | Y | 0.1086 | |
| DP0802.03 | 49 | 60 | 82 | 0.0466 | Y | 0.1762 | |
| DP0802.05 | 49 | 60 | 82 | 0.0466 | Y | 0.1762 | |
| DP0802.06 | 47 | 60 | 78 | 0.1284 | | 0.3988 | |
| DP0802.07 | 51 | 60 | 85 | 0.0266 | Y | 0.1086 | |
| DP0802.08 | 53 | 60 | 88 | 0.0043 | Y | 0.0198 | Y |
| DP0802.09 | 46 | 60 | 77 | 0.2000 | | 0.5557 | |
| DP0802.11 | 51 | 60 | 85 | 0.0147 | Y | 0.0639 | |
| DP0802.12 | 54 | 60 | 90 | 0.0024 | Y | 0.0107 | Y |
| DP0802.13 | 46 | 60 | 77 | 0.2000 | | 0.5557 | |

4) Paraquat Validation Results of OsDN-DTP9 (DP0949) Transgenic Rice

In the first experiment, after paraquat solution treated for seven days, 499 of the 600 OsDN-DTP9 transgenic seedlings (83%) kept green and showed tolerant phenotype, while 112 of the 180 (62%) seedlings from ZH11-TC showed tolerant phenotype, and 136 of the 180 (76%) DP0158 seedlings showed tolerant phenotype. The tolerance rate of all screened OsDN-DTP9 transgenic seedlings was significantly greater than ZH11-TC and DP0158 controls at the construct level.

Further analysis at transgenic line level indicates that nine OsDN-DTP9 transgenic lines had significantly greater tolerance rates than ZH11-TC and two lines had significantly greater tolerance rates than DP0158 control (Table 21). These results demonstrate that OsDN-DTP9 transgenic rice plants had enhanced paraquat tolerance compared to both controls of ZH11-TC and DP0158 rice plants at construct and transgenic line level at seedling stages. OsDN-DTP9 functions in enhancing paraquat tolerance or antioxidative ability of transgenic plants.

TABLE 21

Paraquat tolerance assay of OsDN-DTP9 transgenic rice plants (1st experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0949 (Construct) | 499 | 600 | 83 | 0.0000 | Y | 0.0151 | Y |
| ZH11-TC | 112 | 180 | 62 | | | | |
| DP0158 | 136 | 180 | 76 | | | | |
| DP0949.01 | 50 | 60 | 83 | 0.0047 | Y | 0.2189 | |
| DP0949.02 | 55 | 60 | 92 | 0.0003 | Y | 0.0133 | Y |
| DP0949.06 | 49 | 60 | 82 | 0.0087 | Y | 0.3348 | |
| DP0949.07 | 49 | 60 | 82 | 0.0087 | Y | 0.3348 | |
| DP0949.08 | 49 | 60 | 82 | 0.0087 | Y | 0.3348 | |
| DP0949.11 | 55 | 60 | 92 | 0.0003 | Y | 0.0133 | Y |
| DP0949.12 | 48 | 60 | 80 | 0.0157 | Y | 0.4842 | |
| DP0949.13 | 50 | 60 | 83 | 0.0047 | Y | 0.2189 | |
| DP0949.14 | 45 | 60 | 75 | 0.0786 | | 0.9313 | |
| DP0949.16 | 49 | 60 | 82 | 0.0087 | Y | 0.3348 | |

In the second experiment, the same ten OsDN-DTP9 transgenic lines were tested. Seven days later, 474 of the 588 OsDN-DTP9 transgenic seedlings (81%) kept green and showed tolerant phenotype, while 111 of the 180 (62%) seedlings from ZH11-TC showed tolerant phenotype, and 132 of the 192 (69%) DP0158 seedlings showed tolerant phenotype. The tolerance rate of all screened OsDN-DTP9 transgenic seedlings was significantly greater than ZH11-TC and DP0158 controls at the construct level.

Further analysis at transgenic line level indicates that seven OsDN-DTP9 transgenic lines had significantly greater tolerance rates than ZH11-TC and four lines had significantly greater tolerance rates than DP0158 control (Table 22). These results demonstrate that OsDN-DTP9 transgenic rice plants had enhanced paraquat tolerance compared to both controls of ZH11-TC and DP0158 rice plants at construct and transgenic line level at seedling stages. OsDN-DTP9 play a role in enhancing paraquat tolerance or antioxidative ability of transgenic plants.

5) Paraquat Validation Results of OsWD40-42 (DP0950) Transgenic Rice

In the first experiment, 460 of the 600 transgenic seedlings (77%) kept green and showed tolerant phenotype after treated with 0.8 μM paraquat solutions for 7 days, while 119 of the 180 (66%) seedlings from ZH11-TC showed tolerant phenotype and 134 of the 180 (74%) seedlings from DP0158 showed tolerant phenotype. The tolerance rate of OsWD40-42 transgenic seedlings was significantly higher than ZH11-TC control and higher than DP0158 control.

Analysis at transgenic line level is displayed in Table 23. Five OsWD40-42 transgenic lines had significantly higher tolerance rates than ZH11-TC control. These results show that over-expression OsWD40-42 gene increased the paraquat tolerance or antioxidative ability of the transgenic plants.

TABLE 22

Paraquat tolerance assay of OsDN-DTP9 transgenic rice plants (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0949 (Construct) | 474 | 588 | 81 | 0.0000 | Y | 0.0004 | Y |
| ZH11-TC | 111 | 180 | 62 | | | | |
| DP0158 | 132 | 192 | 69 | | | | |
| DP0949.01 | 51 | 60 | 85 | 0.0021 | Y | 0.0191 | Y |
| DP0949.02 | 51 | 60 | 85 | 0.0021 | Y | 0.0191 | Y |
| DP0949.06 | 42 | 60 | 70 | 0.2506 | | 0.8556 | |
| DP0949.07 | 47 | 60 | 78 | 0.0235 | Y | 0.1606 | |
| DP0949.08 | 45 | 60 | 75 | 0.0676 | | 0.3599 | |
| DP0949.11 | 48 | 60 | 80 | 0.0132 | Y | 0.1001 | |
| DP0949.12 | 48 | 60 | 80 | 0.0132 | Y | 0.1001 | |
| DP0949.13 | 44 | 60 | 73 | 0.1089 | | 0.5025 | |
| DP0949.14 | 54 | 60 | 90 | 0.0004 | Y | 0.0031 | Y |
| DP0949.16 | 44 | 58 | 76 | 0.0008 | Y | 0.0044 | Y |

TABLE 23

Paraquat tolerance assay of OsWD40-42 transgenic rice plants (1st experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0950 (Construct) | 460 | 600 | 77 | 0.0043 | Y | 0.4491 | |
| ZH11-TC | 119 | 180 | 66 | | | | |
| DP0158 | 134 | 180 | 74 | | | | |
| DP0950.01 | 50 | 60 | 83 | 0.0160 | Y | 0.1668 | |
| DP0950.03 | 49 | 60 | 82 | 0.0287 | Y | 0.2614 | |
| DP0950.04 | 45 | 60 | 75 | 0.2064 | | 0.9321 | |
| DP0950.05 | 47 | 60 | 78 | 0.0833 | | 0.5472 | |
| DP0950.09 | 46 | 60 | 77 | 0.1340 | | 0.7319 | |
| DP0950.10 | 48 | 60 | 80 | 0.0498 | Y | 0.3885 | |
| DP0950.12 | 49 | 60 | 82 | 0.0287 | Y | 0.2614 | |
| DP0950.14 | 48 | 60 | 80 | 0.0498 | Y | 0.3885 | |
| DP0950.15 | 42 | 60 | 70 | 0.5810 | | 0.5031 | |
| DP0950.16 | 36 | 60 | 60 | 0.3952 | | 0.0385 | |

In the second experiment, 436 of the 600 transgenic seedlings (73%) kept green and showed tolerant phenotype after treated with 0.8 µM paraquat solutions for 7 days, while 105 of the 180 (58%) seedlings from ZH11-TC showed tolerant phenotype and 107 of the 180 (59%) seedlings from DP0158 showed tolerant phenotype. The tolerance rate of OsWD40-42 transgenic seedlings was significantly higher than ZH11-TC and DP0158 controls.

Analysis at transgenic line level is displayed in Table 24. Four OsWD40-42 transgenic lines had significantly higher tolerance rates than either ZH11-TC or DP0158 controls. These results show that over-expression OsWD40-42 gene increased the paraquat tolerance or antioxidative ability of the transgenic plants. OsWD40-42 plays a role in enhancing paraquat tolerance or antioxidative ability of the transgenic plants.

TABLE 24

Paraquat tolerance assay of OsWD40-42 transgenic rice plants (2nd experiment)

| Line ID | Number of tolerant seedlings | Number of total seedlings | Tolerance rate (%) | CK = ZH11-TC P value | P ≤ 0.05 | CK = DP0158 P value | P ≤ 0.05 |
|---|---|---|---|---|---|---|---|
| DP0950 (Construct) | 436 | 600 | 73 | 0.0003 | Y | 0.0007 | Y |
| ZH11-TC | 105 | 180 | 58 | | | | |
| DP0158 | 107 | 180 | 59 | | | | |
| DP0950.01 | 41 | 60 | 68 | 0.1743 | | 0.2245 | |
| DP0950.03 | 40 | 60 | 67 | 0.2570 | | 0.3234 | |
| DP0950.04 | 53 | 60 | 88 | 0.0002 | Y | 0.0003 | Y |
| DP0950.05 | 47 | 60 | 78 | 0.0080 | Y | 0.0115 | Y |
| DP0950.09 | 39 | 60 | 65 | 0.3642 | | 0.4476 | |
| DP0950.10 | 45 | 60 | 75 | 0.0254 | Y | 0.0355 | Y |
| DP0950.12 | 49 | 60 | 82 | 0.0023 | Y | 0.0034 | Y |
| DP0950.14 | 37 | 60 | 62 | 0.6507 | | 0.7626 | |
| DP0950.15 | 43 | 60 | 72 | 0.0715 | | 0.0962 | |
| DP0950.16 | 42 | 60 | 70 | 0.1136 | | 0.1496 | |

Example 6

Grain Yield of Mature Transgenic Rice Plants Under Well-Watered Conditions

The transgenic rice plants and ZH11-TC and DP0158 rice plants were planted in the paddy field to measure the grain yield under the well-watered conditions. Five transgenic lines from each gene construct were chosen. The T2 seeds were first sterilized, and the germinated seeds were planted in a seedbed field. At 3-leaf stage, the seedlings were transplanted into the testing field with 4 replicates and 40 plants per replicate for each transgenic line, and the 4 replicates were planted in the same block. ZH11-TC and DP0158 seedlings were nearby the transgenic lines in the same block, and were used as controls in the statistical analysis.

The rice plants were managed by normal practice using pesticides and fertilizers. Plant phenotypes were observed and recorded during the experiments. At the end of the growing season, representative plants of each transgenic line were harvested from the middle of the row per line, and grain yield per plant was measured. The grain yield data were statistically analyzed using mixed linear model.

OsABCB12 (DP1169) Transgenic Rice Plants Planted Under Well-Watered Conditions

Five OsABCB12 transgenic rice lines were used. There was no visibly different phenotype between the transgenic rice plants and the control plants. As shown in Table 25, the grain yield per plant of OsABCB12 transgenic rice was significantly greater than that of ZH11-TC and DP0158 controls at the construct level, and three transgenic rice lines showed greater grain yield per plant than controls at the line level. These results show that over-expression of OsABCB12 gene improves the grain yield per plant under well-watered conditions.

TABLE 25

Grain yield analysis of OsABCB12 transgenic rice plants under well-watered conditions

| Line ID | Number of survival plants | Number of harvested plants | Yield per plant (g) | CK = ZH11-TC | | | CK = DP0158 | | |
|---|---|---|---|---|---|---|---|---|---|
| | | | | Diff | P value | P ≤ 0.1 | Diff | P value | P ≤ 0.1 |
| DP1169 (Construct) | 1086 | 888 | 17.96 | 1.00 | 0.079 | Y | 5.55 | 0.000 | Y |
| ZH11-TC | | | 16.97 | | | | | | |
| DP0158 | | | 12.41 | | | | | | |
| DP1169.02 | 211 | 179 | 19.79 | 2.82 | 0.004 | Y | 7.37 | 0.000 | Y |
| DP1169.04 | 215 | 180 | 16.15 | -0.82 | 0.393 | | 3.73 | 0.000 | Y |
| DP1169.09 | 216 | 170 | 15.84 | -1.13 | 0.229 | | 3.43 | 0.000 | Y |
| DP1169.10 | 216 | 179 | 19.39 | 2.42 | 0.009 | Y | 6.98 | 0.000 | Y |
| DP1169.12 | 228 | 180 | 18.66 | 1.69 | 0.083 | Y | 6.24 | 0.000 | Y |

Example 7

Transformation and Evaluation of Maize with Rice Drought Tolerance Genes

Maize plants can be transformed to over-express *Oryza sativa* drought tolerance genes or a corresponding homolog from maize, *Arabidopsis*, or other species. Expression of the gene in the maize transformation vector can be under control of a constitutive promoter such as the maize ubiquitin promoter (Christensen et al. (1989) *Plant Mol. Biol.* 12:619-632 and Christensen et al. (1992) *Plant Mol. Biol.* 18:675-689) or under control of another promoter, such as a stress-responsive promoter or a tissue-preferred promoter. The recombinant DNA construct can be introduced into maize cells by particle bombardment substantially as described in International Patent Publication WO 2009/006276. Alternatively, maize plants can be transformed with the recombinant DNA construct by *Agrobacterium*-mediated transformation substantially as described by Zhao et al. in *Meth. Mol. Biol.* 318:315-323 (2006) and in Zhao et al., Mol. Breed. 8:323-333 (2001) and U.S. Pat. No. 5,981,840 issued Nov. 9, 1999. The *Agrobacterium*-mediated transformation process involves bacterium inoculation, co-cultivation, resting, selection and plant regeneration.

Progeny of the regenerated plants, such as T1 plants, can be subjected to a soil-based drought stress. Using image analysis, plant area, volume, growth rate and color can be measured at multiple times before and during drought stress. Significant delay in wilting or leaf area reduction, a reduced yellow-color accumulation, and/or an increased growth rate during drought stress, relative to a control, will be considered evidence that the gene functions in maize to enhance drought tolerance.

What is claimed is:

1. A method of increasing drought tolerance in a plant, the method comprising:
   (a) expressing in a plant a polynucleotide encoding a polypeptide comprising an amino acid sequence of at least 95% sequence identity to SEQ ID NO: 3 operably linked to a regulatory element, wherein the expression level of the polynucleotide is increased compared to that of a control plant; and
   (b) selecting a plant of part (a) comprising the polynucleotide operably linked to the regulatory element for increased drought tolerance as compared to a control plant not comprising the polynucleotide operably linked to the regulatory element.

2. The method of claim 1, wherein the expression of the polynucleotide is increased by
   expressing in the plant a recombinant DNA construct comprising the polynucleotide sequence operably linked to the regulatory element.

3. A method of enhancing grain yield in a rice plant, the method comprising:
   (a) expressing in a plant a polynucleotide encoding a polypeptide comprising an amino acid sequence of at least 95% sequence identity to SEQ ID NO: 3 operably linked to a regulatory element, wherein the expression level of the polynucleotide is increased compared to that of a control plant; and
   (b) selecting a plant of part (a) comprising the polynucleotide operably linked to the regulatory element for increased yield as compared to a control plant not comprising the polynucleotide operably linked to the regulatory element.

4. The method of claim 3, wherein the expression of the polynucleotide is increased by
   expressing in the plant a recombinant DNA construct comprising the polynucleotide sequence operably linked to the regulatory element.

5. The method of claim 1, wherein the regulatory element is a heterologous regulatory element.

6. The method of claim 5, wherein the heterologous regulatory element is a heterologous promoter.

7. The method of claim 3, wherein the regulatory element is a heterologous regulatory element.

8. The method of claim 7, wherein the heterologous regulatory element is a heterologous promoter.

9. The method of claim 1, wherein said plant is selected from the group consisting of rice, maize, and soybean.

10. The method of claim 3, wherein said plant is selected from the group consisting of rice, maize, and soybean.

11. The method of claim 1, wherein the polynucleotide encodes a polypeptide comprising an amino acid sequence of at least 98% sequence identity to SEQ ID NO: 3.

12. The method of claim 3, wherein the polynucleotide encodes a polypeptide comprising an amino acid sequence of at least 98% sequence identity to SEQ ID NO: 3.

* * * * *